US011590131B2

(12) United States Patent
Shendelman

(10) Patent No.: US 11,590,131 B2
(45) Date of Patent: Feb. 28, 2023

(54) COMPOSITIONS AND METHODS FOR TREATING GALACTOSEMIA

(71) Applicant: Applied Therapeutics, Inc., New York, NY (US)

(72) Inventor: Shoshana Shendelman, New York, NY (US)

(73) Assignee: Applied Therapeutics, Inc., New York, NY (US)

( * ) Notice: Subject to any disclaimer, the term of this patent is extended or adjusted under 35 U.S.C. 154(b) by 0 days.

(21) Appl. No.: 16/634,509

(22) PCT Filed: Jul. 27, 2018

(86) PCT No.: PCT/US2018/044199
§ 371 (c)(1),
(2) Date: Jan. 27, 2020

(87) PCT Pub. No.: WO2019/023648
PCT Pub. Date: Jan. 31, 2019

(65) Prior Publication Data
US 2020/0230139 A1 Jul. 23, 2020

Related U.S. Application Data

(60) Provisional application No. 62/538,443, filed on Jul. 28, 2017.

(51) Int. Cl.
*A61K 31/5025* (2006.01)
*A61K 31/502* (2006.01)
*A61P 3/00* (2006.01)
*C07D 495/04* (2006.01)

(52) U.S. Cl.
CPC ........ *A61K 31/5025* (2013.01); *A61K 31/502* (2013.01); *A61P 3/00* (2018.01)

(58) Field of Classification Search
CPC ..... A61K 31/5025; A61K 31/502; A61P 3/00; C07D 495/04
See application file for complete search history.

(56) References Cited

U.S. PATENT DOCUMENTS

| | | | |
|---|---|---|---|
| 4,868,301 A | 9/1989 | Mylari et al. |
| 4,939,140 A | 7/1990 | Larson et al. |
| 4,954,629 A | 9/1990 | Mylari et al. |
| 4,996,204 A | 2/1991 | Mylari et al. |
| 5,155,259 A | 10/1992 | Suzuki et al. |
| 5,304,557 A | 4/1994 | Mylari |
| 5,677,342 A | 10/1997 | Malamas et al. |
| 5,728,704 A | 3/1998 | Mylari et al. |
| 6,159,976 A | 12/2000 | Lambert et al. |
| 6,544,756 B1 | 4/2003 | Uchida et al. |
| 6,570,013 B2 | 5/2003 | Mylari |
| 6,579,879 B2 | 6/2003 | Mylari |
| 6,696,407 B1 | 2/2004 | Longo et al. |
| 6,849,629 B2 | 2/2005 | Mylari |
| 6,916,824 B1 | 7/2005 | Hua et al. |
| 7,572,910 B2 | 8/2009 | Mylari |
| 8,916,563 B2 | 12/2014 | Wasmuth et al. |
| 9,650,383 B2 | 5/2017 | Wasmuth et al. |
| 9,921,221 B2 | 3/2018 | King et al. |
| 10,052,324 B2 | 8/2018 | Wasmuth et al. |
| 10,150,779 B2 | 12/2018 | Wasmuth et al. |
| 10,639,306 B2 | 5/2020 | Wasmuth et al. |
| 10,647,726 B2 | 5/2020 | Wasmuth et al. |
| 10,870,658 B2 | 12/2020 | Wasmuth et al. |
| 2002/0068740 A1 | 6/2002 | Mylari |
| 2006/0293265 A1 | 12/2006 | Srivastava et al. |
| 2006/0293371 A1 | 12/2006 | Kamiyama |
| 2007/0060533 A1 | 3/2007 | Yoshikawa et al. |
| 2010/0215726 A1 | 8/2010 | Roth |
| 2011/0092566 A1 | 4/2011 | Srivastava et al. |
| 2013/0029983 A1 | 1/2013 | Ballatore et al. |
| 2013/0225592 A1 | 8/2013 | Wasmuth et al. |
| 2014/0113380 A1 | 4/2014 | Lawrence et al. |
| 2015/0018240 A1 | 1/2015 | Jackson et al. |
| 2015/0072989 A1 | 3/2015 | Wasmuth et al. |
| 2015/0079104 A1 | 3/2015 | Zhou et al. |
| 2015/0079105 A1 | 3/2015 | Chambers et al. |
| 2016/0029983 A1 | 2/2016 | Verna et al. |
| 2017/0021629 A1 | 1/2017 | Higuchi |
| 2017/0216291 A1 | 8/2017 | Wasmuth et al. |
| 2017/0216292 A1 | 8/2017 | Wasmuth et al. |
| 2017/0319584 A1 | 11/2017 | Wasmuth et al. |
| 2017/0362237 A1 | 12/2017 | Mylari |
| 2018/0085437 A1 | 3/2018 | Fan |
| 2018/0209997 A1 | 7/2018 | Cohen et al. |
| 2018/0237451 A1 | 8/2018 | Wasmuth et al. |
| 2018/0271865 A1 | 9/2018 | Wasmuth et al. |
| 2018/0312828 A1 | 11/2018 | Liu et al. |
| 2019/0201400 A1 | 7/2019 | Wasmuth et al. |
| 2020/0028345 A1 | 1/2020 | Roy et al. |
| 2020/0131203 A1 | 4/2020 | Shendelman |
| 2020/0230139 A1 | 7/2020 | Shendelman |
| 2020/0268755 A1 | 8/2020 | Wasmuth et al. |
| 2020/0283451 A1 | 9/2020 | Wasmuth et al. |
| 2020/0289512 A1 | 9/2020 | Wasmuth et al. |
| 2021/0284652 A1 | 9/2021 | Wasmuth et al. |
| 2022/0017535 A1 | 1/2022 | Wasmuth |
| 2022/0071880 A1 | 3/2022 | Shendelman |
| 2022/0125890 A1 | 4/2022 | Zuchner et al. |
| 2022/0249624 A1 | 8/2022 | Zuchner et al. |

FOREIGN PATENT DOCUMENTS

| | | |
|---|---|---|
| CA | 1299178 | 4/1992 |
| CA | 2366858 A1 | 10/2000 |
| CN | 101143868 | 3/2008 |
| CN | 102512407 | 6/2012 |
| EP | 0189272 A2 | 7/1986 |

(Continued)

OTHER PUBLICATIONS

Sato et al., Dose-Dependent Prevention of Sugar Cataracts in Galactose-fed Dogs by the Aldose Reductase Inhibitor M79175, Experimental Eye Research, vol. 66, No. 2, pp. 217-222, 1998.*

(Continued)

*Primary Examiner* — Brenda L Coleman
(74) *Attorney, Agent, or Firm* — Hogan Lovells US LLP

(57) ABSTRACT

The disclosure relates to methods for treating galactosemia and manifestations of galactosemia using aldose reductase inhibitors.

29 Claims, 7 Drawing Sheets

(56) References Cited

FOREIGN PATENT DOCUMENTS

| | | |
|---|---|---|
| EP | 0256629 A2 | 2/1988 |
| EP | 0222576 B1 | 5/1989 |
| EP | 0325375 A1 | 7/1989 |
| EP | 0397350 A1 | 11/1990 |
| EP | 0401981 A1 | 12/1990 |
| EP | 0436307 A1 | 7/1991 |
| EP | 2065038 A1 | 6/2009 |
| EP | 3597650 A1 | 1/2020 |
| EP | 3757107 A1 | 12/2020 |
| FR | 2647676 A1 | 7/1990 |
| JP | 2003155274 | 5/2003 |
| WO | 198905791 A1 | 6/1989 |
| WO | 198906651 A1 | 7/1989 |
| WO | 1991009019 A1 | 6/1991 |
| WO | 1995/026347 A1 | 10/1995 |
| WO | 199915529 A1 | 4/1999 |
| WO | 1999050268 A2 | 10/1999 |
| WO | 2000059510 A1 | 10/2000 |
| WO | 2002079198 A1 | 10/2002 |
| WO | 2003061660 A1 | 7/2003 |
| WO | 2008002678 A2 | 1/2008 |
| WO | 2012009553 A1 | 1/2012 |
| WO | 2014113380 A1 | 7/2014 |
| WO | 2017191274 A2 | 11/2017 |
| WO | 2017223179 A1 | 12/2017 |
| WO | 2018090006 A1 | 5/2018 |
| WO | 2018200258 A1 | 11/2018 |
| WO | 2019023648 A1 | 1/2019 |
| WO | 2020040831 A1 | 2/2020 |
| WO | 2020167937 A1 | 8/2020 |
| WO | 2020205846 A1 | 10/2020 |
| WO | 2020227430 A1 | 11/2020 |
| WO | 2021071965 A1 | 4/2021 |
| WO | 2021202523 A1 | 10/2021 |
| WO | 2021222165 A1 | 11/2021 |

OTHER PUBLICATIONS

International Search Report and Written Opinion dated Oct. 24, 2018 for PCT/US2018/044199.

Coelho et al. "Sweet and sour: an update on classic glactosemia" Journal of Inherited Metabolic Disease, Mar. 9, 2017, vol. 40, p. 325-342.

Aydin-Ozemir et al. "Galactosemia and phantom absence seizures" Journal of Pediatric Neurosciences, Dec. 2014, vol. 9, p. 253-256.

Ridel, K. R. et al., "An Updated Review of the Long-Term Neurological Effects of Galactosemia," Pediatric Neurology (2005) 33(3): 153-161.

Grewal et al. "Updates on Aldose Reductase Inhibitors for Management of Diabetic Complications and Non-diabetic Diseases" (Mini-Reviews in Medicinal Chemistry, 2016, vol. 16(2), pp. 120-162, [online], [retrieved Mar. 17, 2022] found in PubMed, RMS: 26349493, doi: 10.2174/1389557515666150909143737).

Chatzopoulou et al. "Novel Aldose Reductase Inhibitors: a patent survey (2006-present)", Expert Opinion on Therapeutic Patents, 2012, vol. 22:11, pp. 1303-1323, p. 1307, Figure 4.

Trippier et al. "Boronic Acids in Medicinal Chemistry: anticancer, antibacterial, and antiviral applications", Med. Chem. Commun. 2010, vol. 1, pp. 183-198, p. 183, col. 1, para 4: pg185 Table 2.

Tianhong Xu et al., "Indomethacin has a potent antiviral activity against SARS COV-2 in vitro and canine coronavirus in vivo" bioRxiv, Apr. 5, 2020, XP055742348, DOI: 10.1101/2020.04.01. 017624 Retrieved from the Internet: URL: https://www.biorxiv.org/content/10.1101/2020.04.01.017624v1.full.pdf p. 5, para 2-3.

Ghosh Sutapa et al. "Recent Advances in Drug Discovery Research Using Structure-Based Virtual Screening Techniques: Examples of Success for Diverse Protein Targets" in "Drug Discovery Research", Jun. 8, 2007, John Wiley & Sons, Inc., Hoboken NJ, USA, XP05514110, ISBN: 978-0-471-67200-5 pp. 24-62, DOI: 10.1002/9780470131862. ch2 Retrieved from the Internet: https://doi.org/10.1002/9780470131862. ch2.

Coyle et al.," A recovered Case of COVID-19 MMyocarditis and ARDS Treated with Corticosteroids, Tocilizumab, and Experimental AT-001", JACC, Case Reports, vol. 2, No. 9, Jul. 15, 2020 [ages 1331-1336, XP009528095, ISSN: 2666-0849, DOI: 10.1016/J. JAC-CAS.2020.04.025, example 4.

Maratha et al., Classical Galactosaemia and CDG, the N-Glycosylation Interface, A review, JIMD Reports, Aug. 9, 2016, vol. 34, pp. 33-42; p. 34.

Li et al., "Decarboxylative borylation", Science, 2017, 356 (6342), 16 pages.

Alexander et al., "(Acyloxy)alkyl carbamates as novel bioreversible prodrugs for amines: increased permeation through biological membranes", J. Med Chem., 31, pp. 318-322 (1988).

Ayres et al., "Synthesis of derivates of cyclobuteno[c]thiophen and attempts to synthesise thiophen analogues of bipheneylene". Tetrahedron, 31, pp. 1755-1760 (1975).

Berge et al., "Pharmaceutical Salts", J. Pharm. Sci., 66(1), pp. 1-19 (1977).

Hu et al., "Efficacy and Safety of aldose reductase inhibitor for the treatment of diabetic cardiovascular autonomic neuropathy: systematic review and meta-analysis", Plos One, 9(2), e87096, pp. 1-11 (2014).

Ramana et al., "Inhibition of aldose reductase prevents growth factor-induced G1-S phase transition through the AKT/phosphoinositide 3-kinase/E2F-1 pathway in human colon cancer cells", Mol Cancer ther., 9(4), pp. 813-824 (2010).

Satoh et al., "Effect of Ranirestat on Sensory and Motor Nerve Function in Japanese Patients with Diabetic Polyneuropathy: A Randomized Double-Blind Placebo-Controlled Study", J. Diabetes Res. 2016, article ID 5383797, 8 pages (2016).

Srivasrava et al., "Aldose reductase inhibition suppressed oxidative stress-induced inflammatory disorders", published in final edited form as: Chem. Biol. Interact, 1991, pp. 330-338 (2011), 19 pages.

Carbone et al., "Structure of Aldehyde reductase in ternary complex with a 5-arylidene-2,4-thiazolidinedione aldose reductase inhibitor", European Journal of Medicinal Chemistry, 45(3):1140-1145, Mar. 31, 2010 available online Dec. 21, 2009 (5 pages).

Hotta et al., "Short Report: Treatment—Long-term clinical effects of epalrestat, an aldose reductase inhibitor, on progression of diabetic neuropathy and other microvascular complications; multiverse epidemiological analysis based on patient background factors and severity of diabetic neuropathy", Diabetic Medicine, 29:1529-1533, 2012 (5 pages).

Hotta et al. "Long-Term Clinical Effects of Epalrestat, an Aldose Reductase Inhibitor, on Diabetic Peripheral Neuropathy", Diabetes Care, 29(7), pp. 1538-1544 (Jul. 2006).

Pubchem, Substance Record for SID 227698804, Available Date: Feb. 12, 2015, Retrieved from the internet: https://pubchem.ncbi.nlm.nih.gov/substance/227698804 (7pages).

Tammali et al., "Inhibitor of Aldose Reductase Prevents Angiogenesis in vitro and in vivo", published in final edited form as: Angiogenesis, 14(2), pp. 209-221 (May 2011) 19 pages.

Li et al., "Redox State-Dependent and Sorbitol Accumulation-Independent Diabetic Albuminuria in Mice with Transgene-Derived Human Aldose Reductase and Sorbitol Dehydrogenase Deficiency", Diabetologia, Feb. 14, 2004, vol. 47, No. 3, pp. 541-548 entire document.

Cortese et al., "Biallelic Mutations in SORD cause a common and Potentially Treatable Hereditary Neuropathy with Implications for Diabetes", Nature Genetics, Articles https://doi.org/10.1038/s41588-020-0615-4, 19 pages. 2020.

International Search Report and Written Opinion PCT/US2018/027960 dated Jul. 11, 2018.

International Search Report and Written Opinion for PCT/US2020/017913 dated Jun. 16, 2020.

International Search Report and Written Opinion for PCT/US2020/025928 dated Jun. 17, 2020.

International Search Report and Written Opinion for PCT/US2020/054607 dated Jan. 28, 2021.

International Search Report and Written Opinion for PCT/US2020/031708 dated Aug. 12, 2020.

International Search Report and Written Opinion for PCT/US2021/024876 dated Jun. 30, 2021.

(56) References Cited

OTHER PUBLICATIONS

International Search Report and Written Opinion for PCT/US2021/029286 dated Aug. 11, 2021.
International Search Report and Written Opinion for PCT/US2011/044038 dated Dec. 6, 2011.
Xu et al., "Indomethacin has a potent antiviral activity against Sars COV-2 in vitro and canine coronavirus in vivo" bioRxiv, Apr. 5, 2020, XP055742348, DOI: 10.1101/2020.04.01.017624 Retrieved from the Internet: URL: https://www.biorxiv.org/content/10.1101/2020.04.01.017624v1.full.pdf p. 5, para 2-3.
Iyer et al. "Repurposing the aldose reductase inhibitor and diabetic neuropathy drug epalrestat for the congenital disorder of glycosylation PMM2-CDG" Dis. Model. Mech. (2019) 12(11). bioRxiv preprint first posted online May 3, 2019; doi: http://dx.doi.org/10.1101/626697.
Lao et al. "Yeast Models of Phosphomannomutase 2 Deficiency, a Congenital Disorder of Glycosylation" G3 (Bethesda, Md.), Feb. 7, 2019, 9(2):413-423.
Zhang et al. "Bioactivity Focus of α-Cyano-4-hydroxycinnamic acid (CHCA) Leads to Effective Multifunctional Aldose Reductase Inhibitors" Sci. Rep. (2016) 6:24942.
Hohman et al. "Probing the Inhibitor-binding site of aldose reductase with site-directed mutagenesis", Eur. J. Biochem 1998, vol. 256, pp. 310-316.
Roy, Thomas M. et al., "The effect of an aldose reductase inhibitor on cardiovascular performance in patients with diabetes melitus", Diabetes Research and Clinical Practice 1990, vol. 10, pp. 91-97.
Mylari, Banavara L. et al., "Novel, Potent Aldose Reductase Inhibitors: 3,4-Dihydro-4-oxo-3-[[5-(trifuoromethyl)-2-benzothiazolyl]-1-phthalazine-acetic Acid (Zopolrestat) and Congeners", J. Med. Chem., 1991, vol. 34, pp. 108-122.
Mylari, Banavara L., et al.,"Potent, Orally Active Aldose Reductase Inhibitors Related to Zopolrestat: Surrogates for Benzothiazole Side Chain", J. Med. Chem., 1992, vol. 35, pp. 457-465.
Hwang et al., "Central role for aldose reductase pathway in myocardial ischemic injury" The FASEB Journal, Aug. 2004, vol. 18, No. 11, pp. 1192-1199.
Cannon, "Chapter Nineteen: Analog Design, "Burger's Medicinal Chemistry and Drug Discovery: fifth edition, vol. 1 Principles and Practice, Wiley-lnterscience, pp. 783-802 (1995).
Kinoshita, "A thirty year journey in the polyol pathway", Exp. Eye. Res., vol. 50, No. 6, pp. 567-573 (1990).
Mylari et al., "Orally active aldose reductase inhibitors: indazoleacetic, oxopyridazineacetic, and oxopyrdopyridazineacetic acid derivatives," J Med. Chem. Vol. 35, pp. 2155-2162 (1992).
Sheridan, "The most common replacements in Drug-like compounds", J. Chem. Inf. Comput. Sci., vol. 42, pp. 103-108 (2002).
Wilson et al., "Refined 1.8 a structure of human aldose reductase comlexed with the potent inhibitor zopolrestat", Proc. Natl. Acad. Sci. USA, vol. 90, No. 21, pp. 9847-9841 (Nov. 1993).
Kalofoutis et al., "Type II diabetes mellitus and cardiovascular risk factors: current therapeutic approaches" Exp. Clin. Cardiol., 2007, vol. 12, No. 1 pp. 17-28.
Zhu, C. "Aldose Reductase Inhibitors as Potential Therapeutics Drugs of Diabetic Complications", Chapter 2 of Diabetes Mellitus—Insights and Perspectives" Jan. 23, 2013,, pp. 17-46", book edited by Oluwafemi O. Oguntibeju, published: Jan. 23, 2013 under CC BY 3.0 License.
Lightman, S. "Does Aldose Reductase have a role in the development of the ocular complications of diabetes?" Eye, 1993, vol. 7, pp. 238-241.
Digiacomao, M. "Synthesis and functional evaluation of novel aldose reductase inhibitors" The Open Medicinal Chemistry Journal, Apr. 2017, vol. 11.
Ramasamy et al., "Aldose reductase and cardiovascular diseades, creating human-like diabetic complications in an experimental model" Circ Res, May 2010, vol. 106, No. 9, pp. 1449-1458.
Nour et al. "Ischemia-Reperfusion Injury in Stroke" Intervent Neurol, 2012, vol. 1, pp. 185-199.
Jacoby et al., "Acute Myocardial Infarction in the Diabetic Patient: Pathophysiology, Clinical course and Prognosis", J. Am. Coll. Cardio., vol. 20, No. 3, pp. 736-744 (1992).
Veves, "Aldose Reductase Inhibitors for the treatment of Diabetic Neuropathy", Contemporary Diabetes: Diabetic Neuropathy: Clinical Management, Second edition, Humana Press, chapter 18, pp. 309-320 (2007).
Beyer-Mears et al., "Glomerular Polyol Accumulation in Diabetes and its Prevention by Oral Sorbinil", Diabetes, Jun. 1984, vol. 33, No. 6, pp. 604-607.
Caliceti et al., "New Insights from Pharmacological Aspects to Clinical Evidences in the Management of Metabolic Disorders", Curr. Med. Chem. (2016) vol. 23, No. 14, pp. 1460-1476.
Cheng et al., "The effect of high glucose and oxidative stress on lens metabolism, aldose reductase, and senile cataractogenesis", Abstract only, Metabolism, Apr. 1986, vol. 35, No. 4 Suppl 1, pp. 10-14.
Cheung et al., "Aldose Reductase Deficiency Prevents Diabetes-Induced Blood-Retinal Barrier Breakdown, Apoptosis, and Glial Reactivation in the Retina of db/db Mice, "Diabetes, Nov. 2005, vol. 54, No. 11 pp. 3119-3125.
Clinical Trials.gov, "Ezetimibe Versus Nutraceuticals in Statin-intolerant Patients (ECLIPSE)", ClinicalTrials.Gov identifier No. NTC01490229, Fisrts received Dec. 8, 2011, 4 pages.
Clinical Trials.gov, "Low-dose Statins, and Nutraceuticals in High-intensity Statin-intolerant Patients (ADHERENCE)", ClinicalTrials.Gov identifier No. NTC02001883, first receiced Nov. 24, 2013, 4 pages.
Gu et al., "Effects of lignans extracted from Eucommia ulmoides and aldose reductase inhibitor epalrestant on hypertensive vascular remodeling", Abstract only, J. Ethnopharmacol, Jan. 17, 2011, vol. 133, No. 1, pp. 6-13.
Hotta et al., "Stratified analyses for selecting appropriate target patients with diabetic peripheral neuropathy for long-term treatment with an aldose reductase inhibitor, epalrestant", Diabet. Med. (2008), vol. 25, No. 7, pp. 818-25.
Johnson et al., "Cardiac Abnormalities in Diabetic Patients with Neuropathy", Diabetes Care, Feb. 2004, vol. 27, No. 2, pp. 448-454.
Kajiwara et al., "Lower incidence of myocardial infarction in type 2 diabetic patients with polyneuropathy who were treated with an aldose reductacse inhibitor (epalrestat): a retrospective study", Presentation Abstract, Presentation No. 1241, 47th EASD Annual Meeting, Lisbon, 2011.
Kasajima et al., "Enhanced in situ expression of aldose reductase in peripheral nerve and renal glomeruli in diabetic patients". Abstract only, Virchows Arch., Jul. 2001, vol. 439, No. 1.
Li et al., "Polyol pathway and modulation of ischemia-reperfusion injury in Type 2 diabetic BBZ rat hearts". Cardiovascular Diabetology, Oct. 28, 2008, vol. 7, No. 33, 11 pages.
Liu et al., "Genetic deficiency of aldose reductase counteracts the development of diabetic nephropathy in C57BL/6 mice", Diabetologia, Jan. 27, 2011, vol. 54, No. 5, pp. 1242-1251.
Marin-Neto et al., "Cardiovascular effects of berberine in patients with severe congestive heart failure," Clin. Cardiol., Apr. 1988, vol. 11, No. 4, pp. 253-260.
Price et al., "Mitogen-Activated Protein Kinase p38 Mediates Reduced Nerve Conduction Velocity in Experimental Diabetic Neuropathy", Diabetes, Jul. 2004, vol. 53, No. 7 pp. 1851-1856.
Schulz et al., "Identification of novel downstream targets of platelet glycoprotein VI activation by differential proteosome analysis: implications for thrombus formation". Blood, May 20, 2010, vol. 115, No. 20, pp. 4102-4110.
Tang et al.," Aldose reductase, oxidative stress, and diabetic mellitus", Frontiers in Pharmacology, May 9, 2012, vol. 3, Article 87, 8 pages.
Tang et al., "Glucose and collagen regulate human platelet activity through aldose reductase induction of thromboxane", The Journal of Clinical Investigation, No. 2011, vol. 121, No. 11 pp. 4462-4476.
Tawata et al., "Anti-platelet action of isoliquiritigenin, an aldose reductase inhibitor in licorice", abstract only, Eur. J. Pharmacol, Feb. 25, 1992, vol. 212, No. 1, pp. 87-92.
Vedantham et al., "Human Aldose Reductase Expression Accelerates Atherosclerosis in Diabetic apoE-/- Mice Reductase", Arteriosler. Thromb. Vasc. Biol. Vol. 31, No. 8 pp. 1805-1813, Aug. 1, 2012.

(56) References Cited

OTHER PUBLICATIONS

Yagihashi et al., "Neuropathy in diabetic mice overexpressing human aldose reductase and effects of aldose Yeductase inhibitor", Abstract only, Brain, Dec. 2001, vol. 124, Pt. 12, pp. 2448-2458.
Zeng et al., "Efficacy and safety of berberine for congestive heart failure secondary to ischemic or idiopathic dilated cardiomyophaty", abstract only, Am. J Cardiol. Jul. 15, 2003, vol. 92, No. 2, pp. 173-176.
Zhou et al., "Neuroprotective effects of berberine on stroke modles in vitro and in vivo", abstract only, Neurosci. Lett., Dec. 5, 2008, vol. 447, No. 1, pp. 31-36.
Lorenzi, "The Polyol Pathway as a Mechanism for Diabetic Retinopathy: Attractive, Elusive and Resilient", Experimental Diabetes Resarch, vol. 2007, Article ID 61038, 10 pages (2007).
Mylari et al., "A Novel Series of Non-Carboxylic Acid, Non-Hydantoin Inhibitors of Aldose Reductase with Potent Oral Activity in Diabetic Rat Models: 6-(5-Chloro-3-methylbenzofuran-2-sulfony)-2H-pyridazin-3-one and Congeners", J. Med. Chem., 48, pp. 6326-6339 (2005).
Antonetti et al., "Vascular Permeability in Experimental Diabetes is Associated with Reduced Endothelial Occludin Content: Vascular Endothelial Growth Factor Decreases Occludin in Retinal Endothlial Cells", Diabetes, 47, pp. 1953-1959 (Dec. 1998).
Hartsock et al., "A Mouse Model of Retinal Ischemia-Reperfusion Injury Through Elevation of Intraocular Pressure", Journal of Visualized Experiments, 113, e54065, 6 pages (2016).
Kamijo, M. et al. "Galactosemia produces ARI-preventable nodal changes similar to those of diabetic neuropathy," Diabetes Research and Clinical Practice (1994) 25:117-129.

\* cited by examiner

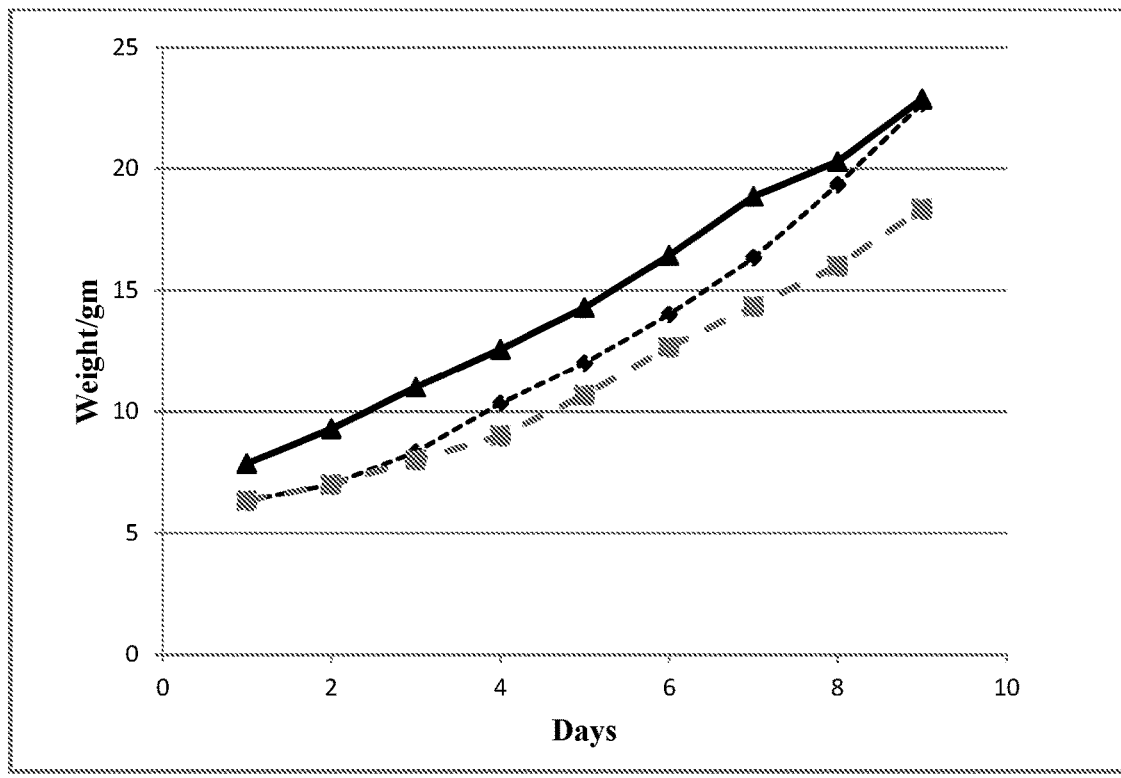
FIG. 1: Impact of drug treatment on weight gain of pups (plotted in grams). Legends: GALT+ (placebo): Solid line, triangle data point; GALT-null (placebo): Dashed grey line; square data point; GALT-null (Compound A): Dashed black line; circle data point.

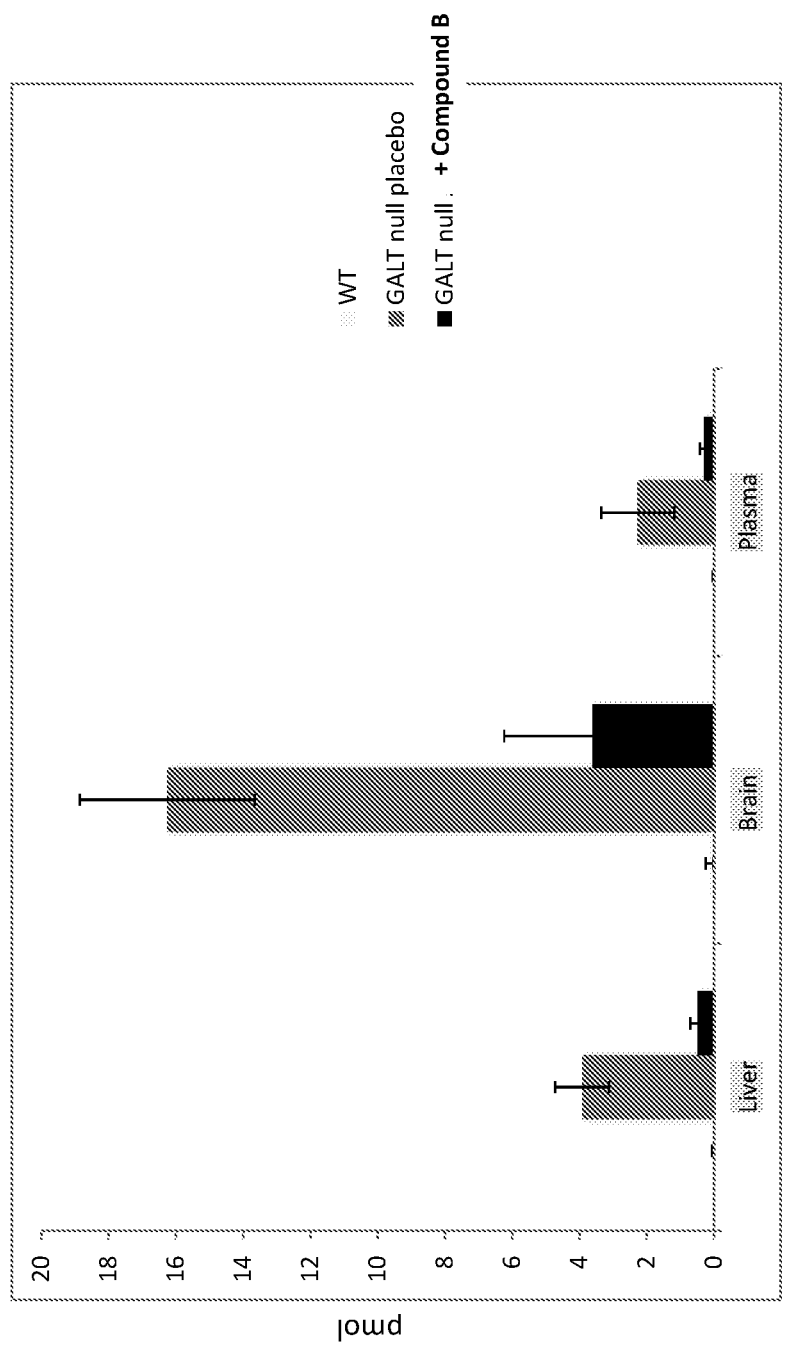
FIG. 3A (galactitol levels at day 10)

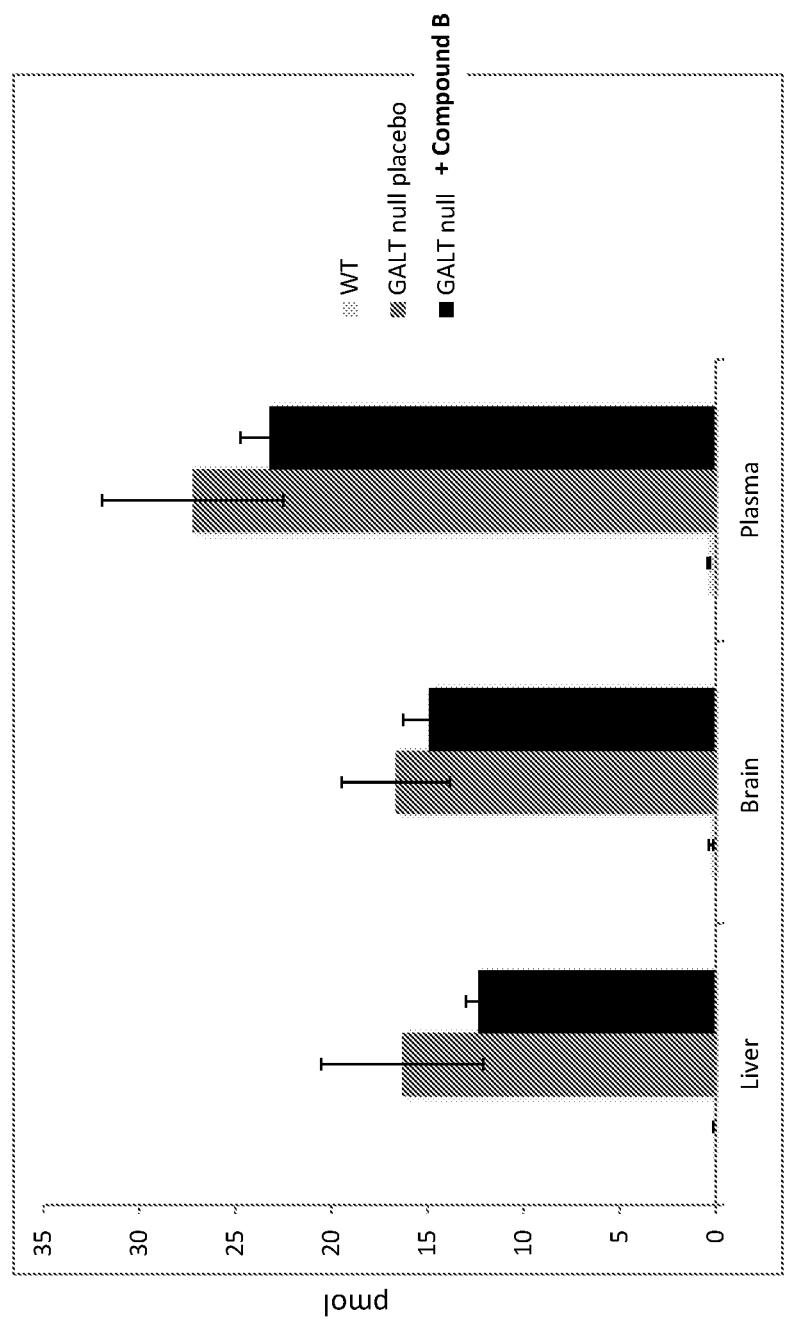
FIG. 3B (galactose levels at day 10)

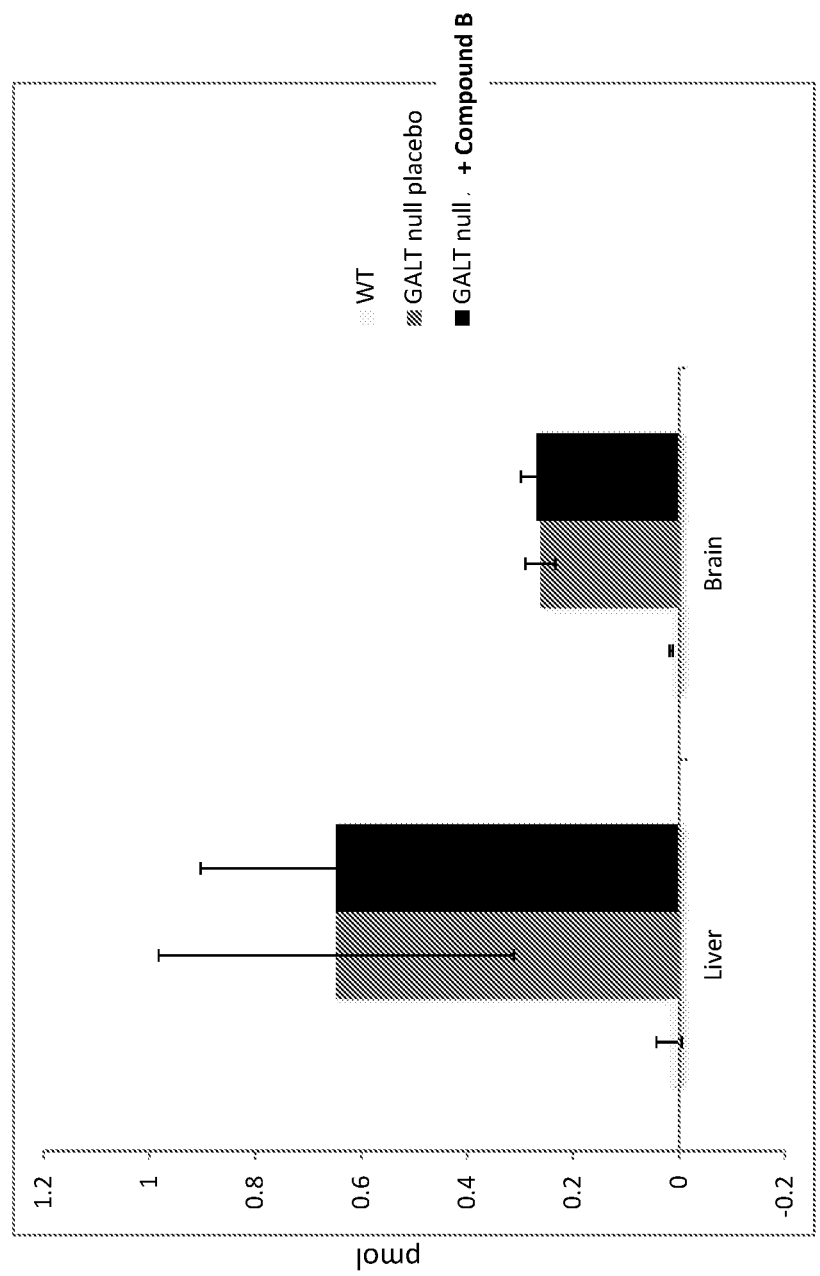
FIG. 3C (galactose-1-phosphate levels at day 10)

COMPOSITIONS AND METHODS FOR TREATING GALACTOSEMIA

RELATED APPLICATIONS

This application is a U.S. National Stage Application of International Application No. PCT/US2018/044199, filed on Jul. 27, 2018, which claims the benefit to U.S. Provisional Application No. 62/538,443, filed Jul. 28, 2017, which is incorporated herein by reference in its entirety.

BACKGROUND

Galactosemia is a metabolic disorder that results from reduced ability or inability to metabolize galactose. The disease is typically caused by deficiency of one or more enzymes involved in the Leloir pathway, including galactose-1-phosphate uridyl transferase (GALT), galactokinase (GALK), and galactose-6-phosphate epimerase (GALE). Deficiency of one or more of these enzymes results in the disruption of the Leloir pathway and accumulation of galactose and certain galactose metabolites, such as galactose 1-phosphate (G1P) and galactonate. In addition, when galactose accumulates, it can become a substrate for aldose reductase (AR), an enzyme in the polyol pathway of glucose metabolism. AR normally catalyzes the reduction of glucose to sorbitol (the first step in the polyol pathway), but can also convert galactose to galactitol when galactose levels are elevated. The accumulation of galactose and galactose metabolites can cause damage to the liver, central nervous system (e.g., brain), kidneys, eyes, and other body systems (Quan-Ma et al., *Am J Dis Child.*, 112(5):477-478, 1966).

Genetic disorders that cause galactosemia can be detected using suitable screening tests (Berry et al. in "Classic Galactosemia and Clinical Variant Galactosemia," *GeneReviews*, Roberta A. Pagon, Eds. University of Washington, Seattle; March, 2017). There currently is no cure for galactosemia and the disease is managed principally through dietary restriction, by eliminating dairy foods and other foods that contain galactose or lactose from the diet. (Welling et al., "International Clinical Guideline for the Management of Classical Galactosemia: Diagnosis, Treatment, and Follow up," *J Inherit Metab Dis*, 40(2):171-176, 2017; Lai et al., *IUBMB Life*, 61(11):1063-74, 2009). However, even when galactosemia is detected early and managed via strict dietary restriction, galactose metabolite levels remain elevated and the majority of patients experience long-term complications such as speech difficulties, cognitive impairment, neurological symptoms and ovarian failure (Schadewaldt et al., *Arch Physiol Biochem.*, 120(5):228-39, 2014; Berry et al., *Mol Genet Metab.*, 81(1):22-30, 2004). However, even with strict dietary control, galactosemia patients are still at high risk of complications, due to endogenous (or internal) synthesis of galactose within the body. Endogenous galactose production has been shown to be highest in infancy and early childhood, but continues at a steady state through adolescence and adulthood. Endogenous production of galactose results in high levels of galactose metabolites in patients even with absolute dietary compliance, and leads to incidence of long-term complications, including central nervous system complications (cognitive, intellectual, speech and motor deficiencies) as well as cataracts in the eye (which may result in partial blindness), and primary ovarian insufficiency (POI) in galactosemic females.

The most common form of galactosemia, type I galactosemia (OMIM #230400) is caused by mutations in GALT, the second enzyme of the Leloir pathway. Mutations of GALK give rise to type II galactosemia (OMIM #230200). Type III galactosemia (OMIM #230350) is caused by mutations in GALE. All three types are autosomal recessive disorders. Based on the degree of functional impairment of the enzymes (biochemical phenotype), genotype, and potential to develop acute and long-term complications, further subtypes of galactosemias have been identified.

The underlying mechanisms of galactosemia pathology are not fully understood, but endogenous production of galactose, and resulting metabolites, is considered to be a significant factor. (Welling et al., *J Inherit Metab Dis*, 40(2): 171-176, 2017). Currently, the only therapy for galactosemia is dietary restriction of galactose, and a life-long galactose-restricted diet is the current standard of care. Although the diet can reverse the acute clinical picture in the newborn, it does not prevent the appearance of long-term complications. No mode of treatment or prevention of any one of the long-term complications exists.

Accordingly, there is a recognized but unmet need for methods for the treatment and/or management of galactosemia.

BRIEF DESCRIPTION OF THE DRAWINGS

FIG. 1 is a graph showing weight gain of wild type rat pups (GALT+), GALT null rat pups, and GALT null rat pups treated with aldose reductase inhibitor (ARI) (Compound A), Weight (g) is plotted on the vertical axis and age (days) is plotted on the horizontal axis.

FIG. 2A shows the results of a qualitative assessment of cataract at day 9 presence/severity score (scale of 0-3) in control (wild-type rats treated with Compound A), and GALT-null rats treated with placebo or Compound A. Score 0 indicates no cataracts present; score 1 indicates cataracts are mild in size and opacity; score 2 indicates cataracts are moderate in size and opacity; and score 3 indicates cataracts are severe in size and opacity. Cataracts were assessed at day 22 of life. FIG. 2B shows the results of a quantitative digital assessment of cataracts in wild type or GALT null rats treated with Compound B or placebo at day 22 of life. FIG. 2C shows the results of a qualitative assessment of cataracts in wild type or GALT null rats treated with Compound B or placebo at day 10 of life. FIG. 2D shows a qualitative assessment of cataracts in wild type or GALT null rats treated with Compound B or placebo at day 22 of life. The qualitative analysis in FIG. 2C and FIG. 2D was performed using the same scoring method as in FIG. 2A.

FIG. 3A-3C are bar charts showing the levels of the metabolites galactitol, galactose, and galactose 1 phosphate in liver, brain or plasma of control (wild-type rats) and GALT-null rats treated with placebo or Compound B. FIG. 3A shows galactitol levels; FIG. 3B shows galactose levels; and FIG. 3C shows galactose-1-phosphate (Gal1P) levels.

SUMMARY

Figure 2A:
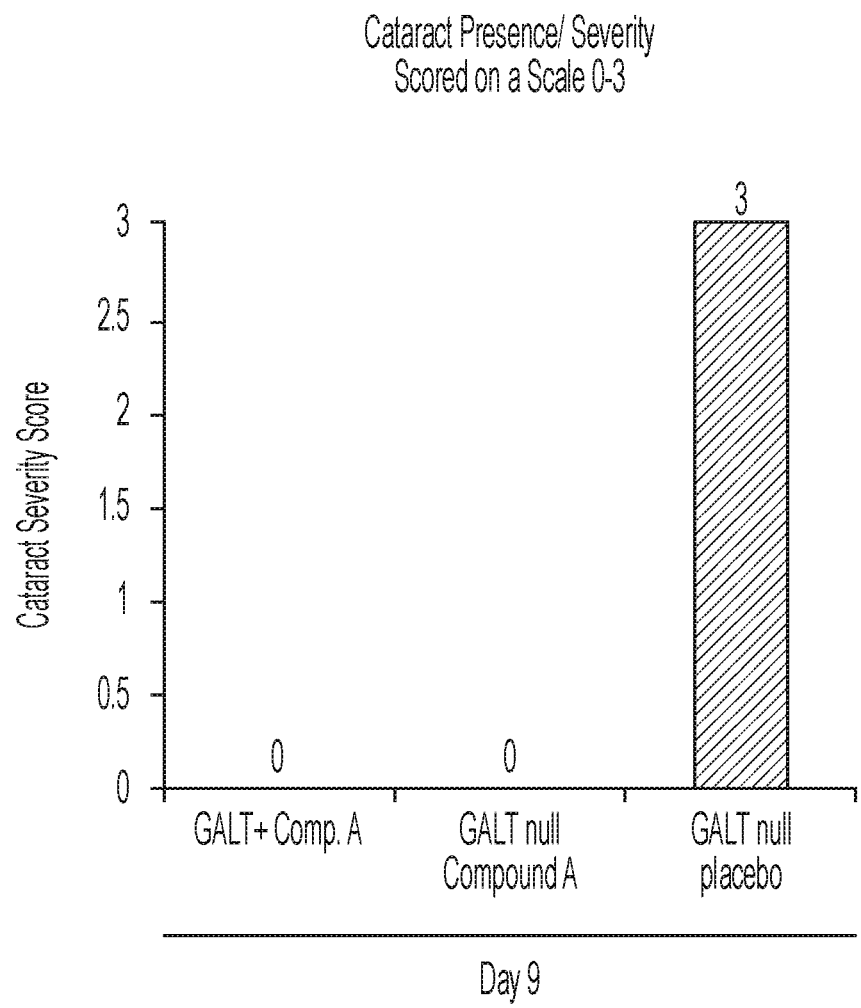
FIGS. 2A-2D are charts showing the effect of aldose reductase inhibitors on cataracts in galactosemic rats.

This disclosure relates to methods for treating galactosemia and treating or preventing complications of galactosemia by administering an therapeutically effective amount of an AR inhibitor to a subject in need thereof. Without wishing to be bound by any particular theory, and as described herein, it is believed that inhibition of AR can reduce or prevent accumulation of galactitol and resulting pathology associated with galactosemia.

In one example, the method for the treatment or prevention of galactosemia (or galactosemia complications) comprises administering to a subject in need thereof an therapeutically effective amount of zopolrestat. In one example, the method for the treatment or prevention of galactosemia (or galactosemia complications) comprises administering to a subject in need thereof an therapeutically effective amount of epalrestat. In one example, the method for the treatment or prevention of galactosemia (or galactosemia complications) comprises administering to a subject in need thereof an therapeutically effective amount of a compound of any one of Formulas I-VI. In some aspects, the AR inhibitor administered is not ponalrestat, epalrestat, sorbinil or sorbinol, imirestat, AND-138, CT-112, zopolrestat, zenarestat, BAL-AR18, AD-5467, M-79175, tolrestat, alconil, statil, berberine or SPR-210.

The subject to be treated in accordance with the methods disclosed herein can have increased alditol levels in blood, urine or intraocular fluid, such as elevated galactitol, myo-inositol or sorbitol levels in blood, urine or intraocular fluid. The subject to be treated in accordance with the methods disclosed herein can have complications or manifestations of galactosemia that include liver cirrhosis, retinal disorder, macular edema, eye cataract, ovarian dysfunction, muscle or nerve dysfunction, retinopathy, neuropathy, cognitive dysfunction, motor ataxia, seizure, pseudomotor cerebrii, speech dysfunction impaired neural conduction or mental retardation. In another embodiment, the disclosure relates to a method of treating or preventing complications associated with galactosemia in a subject in need thereof comprising, administering an therapeutically effective amount of a pharmaceutical composition comprising AR inhibitor and a pharmaceutically acceptable carrier. The disclosure relates to a method of reducing the amount or level of galactitol in a subject with galactosemia, comprising administering a therapeutically effective amount of an aldose reductase inhibitor to the subject.

The disclosure relates to a method for treating cataracts, comprising administering a therapeutically effective amount of an aldose reductase inhibitor to a subject in need thereof. Preferably, the subject in need thereof has galactosemia.

The disclosure relates to a method for treating or preventing cognitive or neurological deficiency associated with galactosemia, comprising administering a therapeutically effective amount of an aldose reductase inhibitor to a subject with galactosemia. In embodiments, the cognitive or neurological deficiency associated with galactosemia is speech dysfunction. In embodiments, the cognitive or neurological deficiency associated with galactosemia is motor ataxia. In embodiments, the cognitive or neurological deficiency associated with galactosemia is cognitive dysfunction. In embodiments, the cognitive or neurological deficiency associated with galactosemia is pseudomotor cerebrii. In embodiments, the cognitive or neurological deficiency associated with galactosemia is seizure.

In another embodiment, the disclosure relates to a method of treating or preventing galactosemia in a subject in need thereof comprising, administering an therapeutically effective amount of (a) a first pharmaceutical composition comprising a compound of Formulas I-VI and a pharmaceutically acceptable carrier; and
(b) a second pharmaceutical composition comprising alponalrestat, epalrestat, sorbinil or sorbinol, imirestat, AND-138, CT-112, zopolrestat, zenarestat, BAL-AR18, AD-5467, M-79175, tolrestat, alconil, statil, berberine or SPR-210 and a pharmaceutically acceptable carrier.

In another embodiment, disclosed herein is a use of an AR inhibitor for inhibiting the production of alditol (e.g., galactitol) for therapy of galactosemia.

In another embodiment, disclosed herein is use of an AR inhibitor for the manufacture of a medicament for treating galactosemia or a clinical manifestation of galactosemia selected from cataracts and primary ovarian insufficiency (POI).

The disclosure also relates to the use of an AR inhibitor (e.g., zopolrestat, epalrestat, compound of any one of Formulas I-VI) for the treatment of galactosemia and/or the treatment and prevention of complications associated with galactosemia.

The disclosure also relates to an AR inhibitor (e.g., zopolrestat, epalrestat, compound of any one of Formulas I-VI) for the manufacture of a medicament for treatment of galactosemia and/or the treatment and prevention of complications associated with galactosemia.

The disclosure also relates to a pharmaceutical formulation for treatment of galactosemia and/or the treatment and prevention of complications associated with galactosemia, that contains an AR inhibitor (e.g., zopolrestat, epalrestat, compound of any one of Formulas I-VI) as an active ingredient.

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete.

This disclosure relates to the use of AR inhibitors for the treatment of galactosemia. The methods described herein are based in part on the inventor's insights into the role of AR activity in the pathophysiology of galactosemia. In normal subjects, AR primarily catalyzes the reduction of glucose to sorbitol (the first step in polyol pathway of glucose metabolism). However, in subjects who have elevated levels of galactose, due to a defective Leloir pathway (e.g., due to deficiency or insufficiency of the associated enzymes) and/or other reasons (e.g., due to over-consumption of lactose, diabetes, endogenous production of galactose), excess galactose is converted into galactitol by the AR. The galactitol produced by this mechanism accumulates in cells because galactitol is not a substrate for the next enzyme in the polyol pathway, sorbitol dehydrogenase. This accumulation of galactitol causes or contributes to the pathophysiological events in galactosemic tissues, such as, hypertonicity, sugar imbalance, oxidative stress, and the like. Accordingly, this disclosure relates to methods for treating or preventing galactosemia or complications of galactosemia by administering an therapeutically effective amount of an AR inhibitor to a subject in need thereof. Without wishing to be bound by any particular theory, it is believed that inhibition of AR can reduce or prevent accumulation of galactitol and resulting pathology and complications associated with galactosemia. These complications may be mediated, in part, via increased synthesis of galactitol and/or increased accumulation of galactitol (e.g., due to deficiency or insufficiency in the enzymes of the Leloir pathway, elevated galactose levels, aberrant AR activity, reduced excretion of galactitol from the tissues (e.g., due to kidney disorders)). Inhibition of aldose reductase can reduce the synthesis and buildup of galactitol in tissues and resulting pathology and complications associated with galactosemia. Accordingly, the present disclosure further relates to the use of galactitol as a biomarker of aldose reductase inhibition, and also, as a biomarker for monitoring the initiation, progression, and manifestation of galactosemia.

Where a range of values is provided in this disclosure, it is intended that each intervening value between the upper and lower limit of that range and any other stated or intervening value in that stated range is encompassed within the disclosure. For example, if a range of 1 µM to 8 µM is stated, it is intended that 2 µM, 3 µM, 4 µM, 5 µM, 6 µM, and 7 µM are also explicitly disclosed, as well as the range of values greater than or equal to 1 µM and the range of values less than or equal to 8 µM.

The singular forms "a," "an," and "the" include plural referents unless the context clearly dictates otherwise. Thus, for example, reference to a "compound of Formula I" includes a single compound as well as two or more of the same or different compounds; reference to an "excipient" includes a single excipient as well as two or more of the same or different excipients, and the like.

The word "about" means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

In order to provide a complete, concise and clear description of the various embodiments, this disclosure includes descriptions of various components, groups of components, ranges and other elements of the broader disclosure. It is intended that such elements can be variously combined to provide additional embodiments of the disclosure. It is also intended that any disclosed features (e.g., substituent, analog, compound, structure, component) including individual members of any disclosed group, including any sub-ranges or combinations of sub-ranges within the group, may be excluded from the disclosure or any embodiments of the disclosure for any reason.

The various embodiments of the present disclosure are further described in detail in the numbered paragraphs below.

I. Methods

In general, the disclosure relates to a method for the treatment of galactosemia (or galactosemia complications), comprising administering to a subject in need thereof an therapeutically effective amount of a compound that inhibits aldose reductase activity. The method is particularly useful for the treatment and/or prevention of complications associated with galactosemia. The compound can be any suitable compound that inhibits AR activity, such as a small molecule compound (e.g., having a size of 5 kDa or less), a biologic agent (e.g., an inhibitory RNA directed against aldose reductase) or a combination thereof. Preferably, the AR inhibitor is a small molecule compound. Suitable small molecule AR inhibitors are known in the art and are disclosed herein. Small molecule AR inhibitors include ponalrestat, sorbinil, sorbinol, imirestat, AND-138, CT-112, zenarestat, BAL-AR18, AD-5467, M-79175, tolrestat, alconil, statil, berberine, SPR-210 zopolrestat, epalrestat, the compounds disclosed in U.S. Pat. Nos. 8,916,563, 9,650, 383, and the compounds disclosed herein. Preferred AR inhibitors for use in the invention include zopolrestat, epalrestat, the compounds disclosed in U.S. Pat. Nos. 8,916,563, 9,650,383, and the compounds disclosed herein. The AR inhibitors can be administered in any molecular suitable form including pharmaceutically acceptable salts, solvates, prodrugs, and compounds that contain stable isotopic forms of one or more atoms, e.g., deuterium in place of hydrogen.

In one example, the method for the treatment of galactosemia (or galactosemia complications), comprises administering to a subject in need thereof an therapeutically effective amount of zopolrestat. Thus, the disclosure provide a method for the treatment of galactosemia and prevention of galactosemia complications in a patient with galactosemia and comprises administered to a subject in need thereof a therapeutically effective amount of zopolrestat.

In one example, the method for the treatment of galactosemia (or galactosemia complications), comprises administering to a subject in need thereof an therapeutically effective amount of epalrestat. Thus, the disclosure provide a method for the treatment of galactosemia and prevention of galactosemia complications in a patient with galactosemia and comprises administered to a subject in need thereof a therapeutically effective amount of epalrestat.

In one example, the method for the treatment of galactosemia (or galactosemia complications), comprises administering to a subject in need thereof an therapeutically effective amount of an aldose reductase, wherein the aldose reductase inhibitor is not ponalrestat, epalrestat, sorbinil or sorbinol, imirestat, AND-138, CT-112, zopolrestat, zenarestat, BAL-AR18, AD-5467, M-79175, tolrestat, alconil, statil, berberine or SPR-210.

In one example, the method for the treatment of galactosemia (or galactosemia complications), comprises administering to a subject in need thereof an therapeutically effective amount of a compound of any one of Formulas I-VI. Thus, the disclosure provide a method for the treatment of galactosemia and prevention of galactosemia complications in a patient with galactosemia and comprises administering to a subject in need thereof a therapeutically effective amount of a compound of any one of Formulas I-VI. In certain examples, the compound that is administered is Compound A or the compound that is administered is Compound B.

As used herein, the term "treating" refers to curative or palliative (e.g., control or mitigate a disease or disease symptoms) therapy. This can include reversing, reducing, arresting or delaying the symptoms, clinical signs, and underlying pathology of galactosemia in a manner to improve or stabilize a subject's condition. The term "preventing" within the context of the present method, refers to a prophylactic treatment of an individual with galactosemia, e.g., to prevent complications (e.g., symptom and clinical signs) associated with galactosemia. For example, a family history or predisposition to diabetes can indicate that the subject is at risk for galactosemia and related complications. Thus, the method can be used for treatment of galactosemia, treatment of complications (e.g., symptoms and clinical signs) of galactosemia, and/or treatment and prevention of complications (e.g., symptoms and clinical signs) of galactosemia.

As used herein "a therapeutically effective amount" is an amount of a compound that is sufficient to achieve the desired therapeutic effect under the conditions of administration, such as an amount that reduces or ameliorates the severity and/or duration of galactosemia or one or more clinical manifestations thereof (e.g., cataracts or primary ovarian insufficiency (POI)), that prevents the advancement of conditions or symptoms related to galactosemia, or enhances or otherwise improves therapeutic effect(s) of another therapy for the treatment or management of galactosemia (e.g., hormonal therapy in the case of POI or surgery in the case of cataracts). A therapeutically effective amount can be an amount that reduces and preferably normalizes the amount or level of galactose or a galactose metabolite, in particular galactitol, in the subject being treated. The actual amount administered can be determined by an ordinarily skilled clinician based upon, for example, the subjects age, weight, sex, general heath and tolerance to drugs, severity of disease, dosage form selected, route of administration and other factors. Typically, the amount of an AR inhibitor that is administered is from about 0.5 to about 60 mg/kg body weight per day, such as from about 1.0 to 10 mg/kg.

In some examples of the practice of the methods disclosed herein, the therapeutically effective amount is an amount sufficient to reduce intracellular aldose reductase activity at least by about 20%, about 30%, about 40%, about 50%, about 60%, about 70%, about 80%, about 90%, about 95%, about 99%, or more, e.g., about 100% (e.g., compared to pre-treatment level). The therapeutically effective amount can be an amount that reduces intracellular galactitol levels at least by about 20%, about 30%, about 40%, about 50%, about 60%, about 70%, about 80%, about 90%, about 95%, about 99%, or more, e.g., about 100% (e.g., compared to pre-treatment level). The therapeutically effective amount can be an amount that reduces plasma galactitol concentration to less than 200 µM, particularly less than 100 µM, especially less than 50 µM, and preferably less than 10 µM in a human subject with galactosemia. Plasma galactitol levels are elevated in untreated classical galactosemia patients (120-500 µmol/l) compared to controls (0.08-0.86 µmol/l). (Jakobs et al., *Eur J Pediatr.*, 154(7 Suppl 2):S50-2, 1995). The therapeutically effective amount can be sufficient to restore a physiological trait that is diminished in galactosemia, e.g., diminished eyesight in the case of cataractic subjects or reduced estrogen levels in a subject with POI. A therapeutically effective amount of an aldose reductase inhibitor can be an amount that is sufficient to normalize galactitol levels in tissues (e.g., liver galactitol levels, brain galactitol levels) or the blood (plasma).

A "subject" can be any animal, particularly a mammal, and including, but by no means limited to, humans, domestic animals, such as feline or canine subjects, farm animals, such as but not limited to bovine, equine, caprine, ovine, avian and porcine subjects, wild animals (whether in the wild or in a zoological garden), research or laboratory animals, such as mice, rats, rabbits, goats, sheep, pigs, dogs, cats, etc., avian species, such as chickens, turkeys, songbirds, and the like. Preferably, the "subject" is a human who is predisposed to (due to genetic aberration) or has been diagnosed with galactosemia. Typically, a human subject to be treated using the methods disclosed herein is diagnosed with galactosemia as a new born through enzymatic or genetic screening, and has deficiency in GALT activity, GALK activity or GALE activity.

This disclosure also relates to the prophylaxis or treatment of at least one clinical feature or complication of galactosemia in a subject. Representative clinical features or complications which can be present in children, adolescents or adults, include, e.g., liver dysfunction, susceptibility to infections, failure to thrive, cataracts, retinopathy, neuropsychological and ovarian problems. For example, the disclosure relates to treatment of at least one trait of galactosemic subjects selected from jaundice (incidence: 74% of subjects), vomiting (47% of subjects), hepatomegaly (43% of subjects), failure to thrive (29% of subjects), poor feeding (23% of subjects), lethargy (16% of subjects), diarrhea (12% of subjects), sepsis (10% of subjects), more specifically, *E. coli* sepsis (76% of sepsis), coagulopathy, ascites, seizures, hepatomegaly, hypotonia, edema, full fontanelle, encephalopathy, and excessive bruising or bleeding, primary ovarian insufficiency and premature ovarian failure (POF). Additionally, galactosemic patients may have low bone density. Preferably, the clinical feature is lenticular cataracts, retinopathy, or ovarian dysfunction (e.g., primary ovarian insufficiency (POI) or premature ovarian failure (POF)). See, Berry et al. "Classic Galactosemia and Clinical Variant Galactosemia," in GeneReviews, Pagon R A, Adam M P, Ardinger H H, et al. Eds. University of Washington, Seattle, 2017.

Patients with galactosemia can experience long-term neurological and cognitive complications, even when the disease is diagnosed early and is managed with a galactose-restricted diet. Such complications are variable, and include, below average IQ, impaired executive function, tremor, ataxia, dysarthria, apraxia of speech, depression and anxiety. Accordingly, additional preferred clinical features of galactosemia that can be treated or prevented using the methods described herein are neurological and cognitive deficiencies, such as central nervous system deficiencies including speech dysfunctions (e.g., delayed or impaired speech), motor ataxia, seizure, pseudomotor cerebrii and cognitive dysfunction (e.g., low IQ (IQ below about 85)).

In a particular aspect, the disclosure relates to a method for the treatment of a clinical feature or complication of galactosemia and comprises administering to a subject in need thereof an therapeutically effective amount of zopolrestat.

In one example, the disclosure relates to a method for the treatment of a clinical feature or complication of galactosemia and comprises administering to a subject in need thereof an therapeutically effective amount of epalrestat.

In one example, the disclosure relates to a method for the treatment of a clinical feature or complication of galactosemia and comprises administering to a subject in need thereof an therapeutically effective amount of a compound of any one of Formulas I-VI.

In embodiments, the clinical feature or complication of galactosemia to be treated or prevented is retinopathy or cataracts. Presenile cataracts are a common complication in patients with galactosemia, and in particular embodiments, the method is a method for treating cataracts. The cataracts can be subcapsular cataracts occurring at the back of the lens, nuclear cataracts which form in the central zone (nucleus) of the lens, and cortical (spoke-like) cataracts affecting the lens cortex. The methods are also useful in the treatment of cataracts that have been or are being treated with surgery, cataracts that occur after surgical removal of an existing opacified lens, i.e., secondary cataracts, cataracts that occur after retinal detachment and surgery to repair the retinal detachment, cataracts associated with trauma to the eye or head, cataracts associated with tumors, cataracts associated with exposure to radiation, and cataracts associated with sugar toxicity. The present methods are also useful in the prophylactic treatment of cataracts resulting from systemic disorders, for example, but not limited to, galactosemia.

In embodiments, the clinical feature or complication of galactosemia to be treated or prevented is a long-term neurological and cognitive complication of galactosemia. Patients with galactosemia can experience long-term neurological and cognitive complications, even when the disease is diagnosed early and is managed with a galactose-restricted diet. Such complications are variable, and include below average IQ, impaired executive function, tremor, ataxia, dysarthria, apraxia of speech, depression and anxiety.

In embodiments, the clinical feature or complication of galactosemia to be treated or prevented is primary ovarian insufficiency (POI) or premature ovarian failure (POF), or a symptom related thereto. The method comprises administering to a subject in need thereof, a compound of the disclosure or a composition containing the compound. POI is characterized by dysfunctional ovaries (e.g., inability to produce estrogen and other hormones that are important to reproductive health). Galactosemia is one of the few known causes of POI and almost all women with galactosemia have POI or develop it at some point in their lives. Women with POI may be more likely to get the bone disease osteoporosis or have problems with their hearts and POI can also cause infertility. See, Fridovich-Keil et al., *J Inherit Metab Dis.* 34(2): 357-366, 2011. Symptoms or traits associated with POI include, e.g., delayed onset of period, sudden stoppage or disruption in period, malformation of breasts, hot flashes, affect disorders, e.g., mood swings or irritability, vaginal dryness, and/or inability to sleep.

In some aspects, the disclosure relates to a method for reducing the amount or level of galactitol in a subject, comprising administering to a subject in need thereof an therapeutically effective amount of a compound that inhibits aldose reductase activity. The method can be used to reduce galactitol in tissues, such as liver, brain, eye, retina, and/or in the circulation (e.g., blood or plasma) and/or in urine. Preferably, the galactitol levels are normalized. Galactose levels can be elevated in patients with galactosemia, and preferably, the method of reducing galactitol does not cause further elevation of galactose levels. Normal amounts or levels of galactitol are the amounts or levels present in health subjects who are not on a restricted diet. Such normal amounts or levels are well known and shown in Table 1.

In embodiments, the clinical feature or complication of galactosemia to be treated or prevented is retinopathy or cataracts. Presenile cataracts are a common complication in patients with galactosemia, and in particular embodiments, the method is a method for treating cataracts. The cataracts can be subcapsular cataracts occurring at the back of the lens, nuclear cataracts that form in the central zone (nucleus) of the lens, and cortical (spoke-like) cataracts affecting the lens cortex. The methods are also useful in the treatment of cataracts that have been or are being treated with surgery, cataracts that occur after surgical removal of an existing opacified lens, i.e., secondary cataracts, cataracts that occur after retinal detachment and surgery to repair the retinal detachment, cataracts associated with trauma to the eye or head, cataracts associated with tumors, cataracts associated with exposure to radiation, and cataracts associated with sugar toxicity. The present methods are also useful in the prophylactic treatment of cataracts resulting from systemic disorders, for example, but not limited to, galactosemia.

In a particular aspect, the disclosure relates to a method for the treatment or prevention of cataracts and comprises administering to a subject in need thereof a therapeutically effective amount of zopolrestat.

In one example, the disclosure relates to a method for the treatment or prevention of cataracts and comprises administering to a subject in need thereof a therapeutically effective amount of epalrestat.

In one example, the disclosure relates to a method for the treatment or prevention of cataracts and comprises administering to a subject in need thereof a therapeutically effective amount of a compound of any one of Formulas I-VI. In certain examples, the compound that is administered is Compound A or the compound that is administered is Compound B.

Preferably, the patient in need of therapy for the treatment or prevention of cataracts has galactosemia.

In embodiments, the clinical feature or complication of galactosemia to be treated or prevented is a long-term neurological and cognitive complication of galactosemia. Patients with galactosemia can experience long-term neurological and cognitive complications, even when the disease is diagnosed early and is managed with a galactose-restricted diet. Such complications are variable, and include below average IQ, impaired executive function, tremor, ataxia, dysarthria, apraxia of speech, depression and anxiety.

In a particular aspect, the disclosure relates to a method for the treatment or prevention of neurological and cognitive deficiencies associated with galactosemia and comprises administering to a subject with galactosemia a therapeutically effective amount of zopolrestat. In particular embodiments, the neurological or cognitive deficiency associated with galactosemia is speech dysfunction, such as delayed speech or impaired speech. In particular embodiments, the neurological or cognitive deficiency associated with galactosemia is motor ataxia. In particular embodiments, the neurological or cognitive deficiency associated with galactosemia is cognitive dysfunction, such as low IQ. In particular embodiments, the neurological or cognitive deficiency associated with galactosemia is pseudomotor cerebrii. In particular embodiments, the neurological or cognitive deficiency associated with galactosemia is seizure.

In one example, the disclosure relates to a method for the treatment or prevention of neurological and cognitive deficiencies associated with galactosemia and comprises administering to a subject with galactosemia a therapeutically effective amount of epalrestat. In particular embodiments, the neurological or cognitive deficiency associated with galactosemia is speech dysfunction, such as delayed speech or impaired speech. In particular embodiments, the neurological or cognitive deficiency associated with galactosemia is motor ataxia. In particular embodiments, the neurological or cognitive deficiency associated with galactosemia is cognitive dysfunction, such as low IQ. In particular embodiments, the neurological or cognitive deficiency associated with galactosemia is pseudomotor cerebrii. In particular embodiments, the neurological or cognitive deficiency associated with galactosemia is seizure.

In one example, the disclosure relates to a method for the treatment or prevention of neurological and cognitive deficiencies associated with galactosemia and comprises administering to a subject with galactosemia a therapeutically effective amount of a compound of any one of Formulas I-VI. In certain examples, the compound that is administered is Compound A or the compound that is administered is Compound B. In particular embodiments, the neurological or cognitive deficiency associated with galactosemia is speech dysfunction, such as delayed speech or impaired speech. In particular embodiments, the neurological or cognitive deficiency associated with galactosemia is motor ataxia. In particular embodiments, the neurological or cognitive deficiency associated with galactosemia is cognitive dysfunction, such as low IQ. In particular embodiments, the neurological or cognitive deficiency associated with galactosemia is pseudomotor cerebrii. In particular embodiments, the neurological or cognitive deficiency associated with galactosemia is seizure.

In embodiments, the clinical feature or complication of galactosemia to be treated or prevented is primary ovarian insufficiency (POI) or premature ovarian failure (POF), or a symptom related thereto. The method comprises administering to a subject in need thereof, a compound of the disclosure or a composition containing the compound. POI is characterized by dysfunctional ovaries (e.g., inability to produce estrogen and other hormones, which are important to reproductive health). Galactosemia is one of the few known causes of POI and almost all women with galactosemia have POI or develop it at some point in their lives. Women with POI may be more likely to get the bone disease osteoporosis or have problems with their hearts and POI can cause infertility. See, Fridovich-Keil et al., *J Inherit Metab Dis.* 34(2): 357-366, 2011. Symptoms or traits associated with POI include, e.g., delayed onset of period, sudden stoppage or disruption in period, malformation of breasts, hot flashes, affect disorders, e.g., mood swings or irritability, vaginal dryness, and/or inability to sleep.

In a particular aspect, the disclosure relates to a method for the treatment or prevention of POI or POF and comprises administering to a subject with galactosemia a therapeutically effective amount of zopolrestat.

In one example, the disclosure relates to a method for the treatment or prevention of POI or POF and comprises administering to a subject with galactosemia a therapeutically effective amount of epalrestat.

In one example, the disclosure relates to a method for the treatment or prevention of POI or POF and comprises administering to a subject with galactosemia a therapeutically effective amount of a compound of any one of Formulas I-VI. In certain examples, the compound that is administered is Compound A or the compound that is administered is Compound B.

In some aspects, the disclosure relates to a method for reducing the amount or level of galactitol in a subject, comprising administering to a subject in need thereof an therapeutically effective amount of a compound that inhibits aldose reductase activity. The method can be used to reduce galactitol in tissues, such as liver, brain, eye, retina, and/or in the circulation (e.g., blood or plasma) and/or in urine. Preferably, the galactitol levels are normalized. Galactose levels can be elevated in patients with galactosemia, and preferably, the method of reducing galactitol does not cause further elevation of galactose levels. Normal amounts or levels of galactitol are the amounts or levels present in health subjects who are not on a restricted diet. Such normal amounts or levels are well known and shown in

TABLE 1

Galactitol and Galactose levels (micro Molar) in Healthy Subjects (unrestricted diet)*

|  | Galactose | Galactitol |
|---|---|---|
| Plasma | ~0.1–~6.3 | Absent to trace |
| Erythrocytes |  | ~0.3–~1.3 |
| Urine | ~2–~4 | Absent to~50 |
| Whole Blood | Absent to~250 |  |

*See, Palmieri M, et al., Urine and Plasma Galactitol in Patients with Galactose-1-Phosphate Uridyltransferase Deficiency Galactosemia. Metabolism 1999; 48; 10:1294-1302; Yager CT, et al, Galactitol and galactonate in red blood cells of galactosemic patients. Molecular Genetics and Metabolism 2003; 80:283-289; Hennerman et al., Features and outcome of galactokinase deficiency in children diagnosed by newborn screening. 2011, J. Inherit Metab. Dis. 34:399-407; and Schadewaldt P, et al., Endogenousn galactose formation in galactose-1-phosphate uridyltransferase deficiency. 2014, Archives of Physiology and Biochemistry 120(5):228-239.

In a particular aspect, the disclosure relates to a method for reducing, and preferably normalizing, the amount or level of galactitol in a subject with galactosemia and comprises administering to a subject in need thereof a therapeutically effective amount of zopolrestat.

In one example, the disclosure relates to a method for reducing, and preferably normalizing, the amount or level of galactitol in a subject with galactosemia and comprises administering to a subject in need thereof a therapeutically effective amount of epalrestat.

In one example, the disclosure relates to a method for reducing, and preferably normalizing, the amount or level of galactitol in a subject with galactosemia and comprises administering to a subject in need thereof a therapeutically effective amount of a compound of any one of Formulas I-VI. In certain examples, the compound that is administered is Compound A or the compound that is administered is Compound B.

In some embodiments, the aforementioned methods are carried out by administering a formulation comprising a single dosage or single administration (e.g., as a single injection or deposition) of one or more AR inhibitors. Alternatively, the methods are carried out by administering formulations that are adapted for administration once daily, twice daily, three times daily or four times daily to a subject in need thereof for a period of from about 2 to about 28 days, or from about 7 to about 10 days, or from about 7 to about 15 days, or longer. In some embodiments, the methods are carried out by administering formulations that are adapted for chronic administration. In yet other embodiments, the methods are carried out by administering formulations that are adapted for administration over the course of several weeks, months, years or decades. In still other embodiments, the methods are carried out by administering formulations that are adapted for administration over the course of several weeks. In still other embodiments, the methods are carried out by administering formulations that are adapted for administration over the course of several months. In still other embodiments, the methods are carried out by administering formulations that are adapted for administration over the course of several years. In still other embodiments, the methods are carried out by administering formulations that are adapted for administration over the course of several decades.

II. AR Inhibitors

Suitable small molecule AR inhibitors are known in the art and are disclosed herein. Small molecule AR inhibitors include ponalrestat, sorbinil, sorbinol, imirestat, AND-138, CT-112, zenarestat, BAL-AR18, AD-5467, M-79175, tolrestat, alconil, statil, berberine, SPR-210, zopolrestat, epalrestat, the compounds disclosed in U.S. Pat. Nos. 8,916,563, 9,650,383, WO2012/009553 and the compounds disclosed herein. Preferred AR inhibitors for use in the invention zopolrestat, epalrestat, the compounds disclosed in U.S. Pat. Nos. 8,916,563, 9,650,383, WO 2017/038505 and the compounds disclosed herein. The disclosures of U.S. Pat. Nos. 8,916,563, 9,650,383, WO 2012/009553, and WO 2017/038505 are incorporated by reference herein in their entirety, and disclose compounds that are suitable for use in the methods described herein.

AR Inhibitors of Formulas I and II

In one example, the AR inhibitor is a compound of Formula (I) or pharmaceutically acceptable salts, prodrugs and solvates thereof,

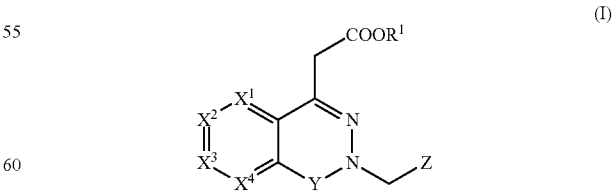

(I)

wherein,
$R^1$ is H, $(C_1-C_6)$-alkyl, $(C_1-C_6)$-hydroxyalkyl, or $(C_1-C_6)$-aminoalkyl;
$X^1$ is N or $CR^3$;
$X^2$ is N or $CR^4$;
$X^3$ is N or $CR^5$;

$X^4$ is N or $CR^6$; with the proviso that two or three of $X^1$, $X^2$, $X^3$, or $X^4$ are N;

Y is a bond, C=O, C=S, C=NH, or C=N($C_1$-$C_4$)-alkyl;

Z is

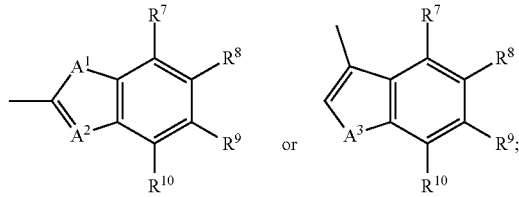

$A^1$ is $NR^{11}$, O, S or $CH_2$;
$A^2$ is N or CH;
$A^3$ is $NR^{11}$, O, or S;
$R^3$ through $R^{10}$ are independently hydrogen, halogen, cyano, acyl, haloalkyl, haloalkoxy, haloalkylthio, trifluoroacetyl, ($C_1$-$C_4$)-alkyl, ($C_1$-$C_4$)-alkoxy, ($C_1$-$C_4$)-alkylthio, ($C_1$-$C_4$)-alkylsulfinyl, or ($C_1$-$C_4$)-alkylsulfonyl; or two of $R^3$ through $R^6$ or two of $R^7$ through $R^{10}$ taken together are ($C_1$-$C_4$)-alkylenedioxy; and
$R^{11}$ is hydrogen, $C_1$-$C_4$ alkyl, or C(O)O—($C_1$-$C_4$)-alkyl.

It will be recognized by those of skill in the art that the designation of Z is

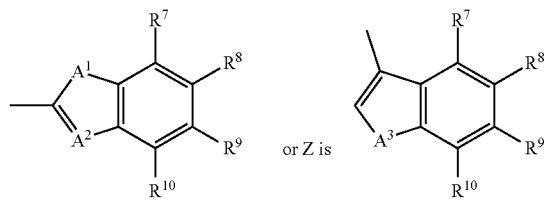

indicates that when Z is

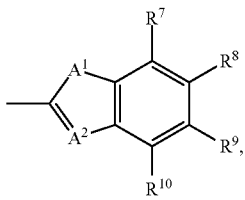

the compounds of formula (I) encompass

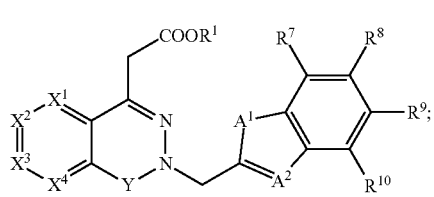

and when Z is

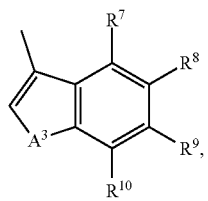

the compounds of formula (I) encompass

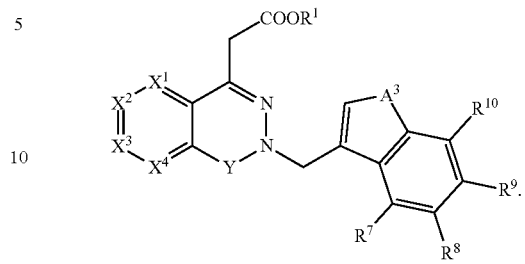

In certain embodiments, $R^1$ is hydrogen or ($C_1$-$C_6$)-alkyl. In certain embodiments, $R^1$ is hydrogen. In certain embodiments, $R^1$ is ($C_1$-$C_6$)-alkyl. In certain embodiments, $R^1$ is tert-butyl.

In certain embodiments, $R^3$ through $R^{10}$ are independently hydrogen, halogen or haloalkyl. In certain embodiments, $R^3$ through $R^{10}$ are independently hydrogen, halogen or trihaloalkyl.

In certain embodiments, $R^3$ through $R^6$ are hydrogen.

In certain embodiments, R through $R^0$ are independently hydrogen, halogen or haloalkyl. In certain embodiments, R through $R^{10}$ are independently hydrogen, halogen or trihaloalkyl.

In certain embodiments, $R^7$ and $R^{10}$ are hydrogen.

In certain embodiments, $R^8$ is hydrogen, halogen or haloalkyl. In certain embodiments, $R^8$ is hydrogen. In certain embodiments, $R^8$ is halogen. In certain embodiments, $R^8$ is haloalkyl.

In certain embodiments, $R^9$ is hydrogen, halogen or haloalkyl. In certain embodiments, $R^9$ is hydrogen. In certain embodiments, $R^9$ is halogen. In certain embodiments, $R^9$ is haloalkyl.

In certain embodiments, Y is C=O, C=S, C=NH, or C=N($C_1$-$C_4$)-alkyl. In certain embodiments, Y is C=O or C=S. In certain embodiments, Y is C=O. In certain embodiments, Y is C=S. In certain embodiments, Y is C=NH, or C=N($C_1$-$C_4$)-alkyl.

In certain embodiments, $A^1$ is $NR^{11}$, S or $CH_2$. In certain embodiments, $A^1$ is $NR^{11}$ or O. In certain embodiments, $A^1$ is $NR^{11}$ or S. In certain embodiments, $A^1$ is $NR^{11}$. In certain embodiments, $A^1$ is O. In certain embodiments, $A^1$ is S.

In certain embodiments, $A^2$ is N or CH. In certain embodiments, $A^1$ is N. In certain embodiments, $A^1$ is CH.

In certain embodiments, $A^3$ is O or S. In certain embodiments, $A^3$ is O. In certain embodiments, $A^3$ is S.

In certain embodiments, $X^1$ and $X^4$ are nitrogen.
In certain embodiments, $X^1$ and $X^2$ are nitrogen.
In certain embodiments, $X^1$ and $X^3$ are nitrogen.
In certain embodiments, $X^2$ and $X^3$ are nitrogen.
In certain embodiments, $X^2$ and $X^4$ are nitrogen.
In certain embodiments, $X^3$ and $X^4$ are nitrogen.
In certain embodiments, Z is

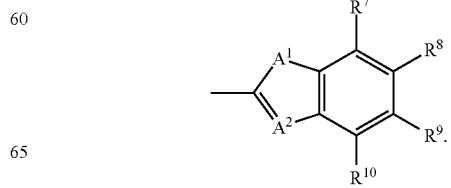

In certain embodiments, Z is

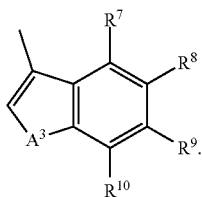

In certain embodiments, $R^1$ is hydrogen or $(C_1-C_6)$-alkyl;
$X^1$ and $X^4$ are N;
$X^2$ is $CR^4$;
$X^3$ is $CR^5$;
Y is C=O;
Z is

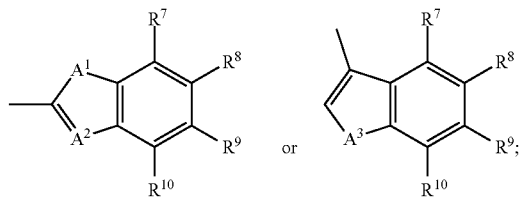

$A^1$ is $NR^{11}$, O, or S;
$A^2$ is N;
$A^3$ is O, or S;
$R^4$ and $R^5$ are hydrogen;
$R^7$ through $R^{10}$ are independently hydrogen, halogen, cyano, acyl, haloalkyl, haloalkoxy, haloalkylthio, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkylsulfonyl; and
$R^{11}$ is hydrogen, $C_1-C_4$ alkyl, or C(O)O—$(C_1-C_4)$-alkyl.
In certain embodiments, $R^1$ is hydrogen or tert-butyl;
$X^1$ and $X^4$ are N;
$X^2$ is $CR^4$;
$X^3$ is $CR^5$;
Y is C=O;
Z is

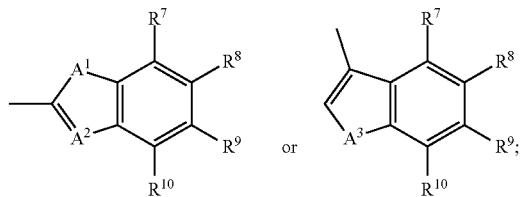

$A^1$ is $NR^{11}$, O or S;
$A^2$ is N;
$A^3$ is O or S;
$R^4$ and $R^5$ are hydrogen;
$R^7$ through $R^{10}$ are independently hydrogen, halogen, or haloalkyl; and
$R^{11}$ is hydrogen, $(C_1-C_4)$-alkyl, or C(O)O-tert-butyl.
In certain embodiments, $R^1$ is hydrogen or tert-butyl;
$X^1$ and $X^4$ are N;
$X^2$ is CH;
$X^3$ is CH;
Y is C=O;
Z is

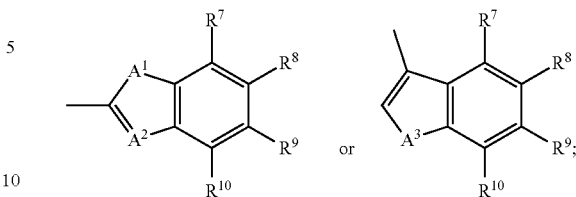

$A^1$ is $NR^{11}$, O or S;
$A^2$ is N;
$A^3$ is O or S;
$R^7$, $R^8$ and $R^{10}$ are independently hydrogen, halogen, or haloalkyl;
$R^9$ is halogen, or haloalkyl; and
$R^{11}$ is hydrogen or methyl.
In certain embodiments, $R^1$ is hydrogen or tert-butyl;
$X^1$ and $X^4$ are N;
$X^2$ is CH;
$X^3$ is CH;
Y is C=O;
Z is

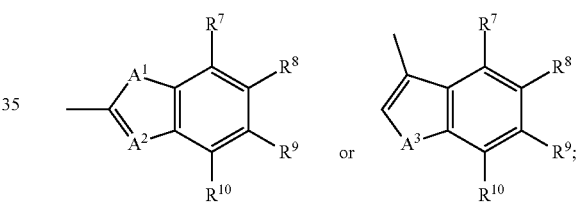

$A^1$ is $NR^1$, O or S;
$A^2$ is N;
$A^3$ is O or S;
$R^7$, $R^8$ and $R^{10}$ are independently hydrogen, halogen, or haloalkyl;
$R^9$ is chlorine, or trifluoromethyl; and
$R^{11}$ is hydrogen or methyl.
In certain embodiments, the AR inhibitor is a compound of Formula (II) or pharmaceutically acceptable salt or solvate thereof:

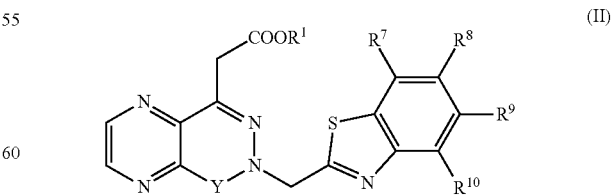

Wherein $R^1$, $R^7$-$R^9$ and Y are as described in Formula I, and preferable wherein $R^1$ is hydrogen or $(C_1-C_6)$-alkyl and Y is C=O. Exemplary compounds of Formula II include the following and salts thereof:

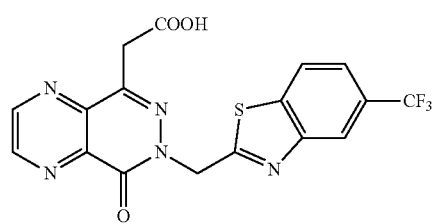

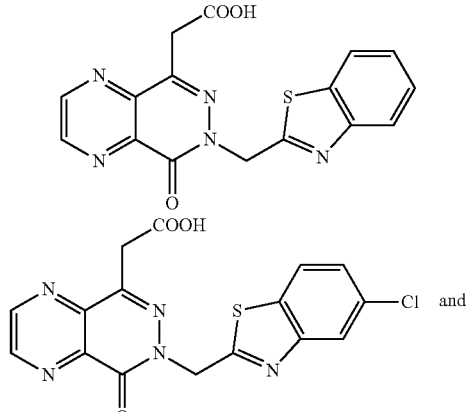

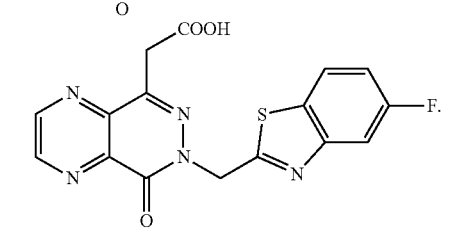

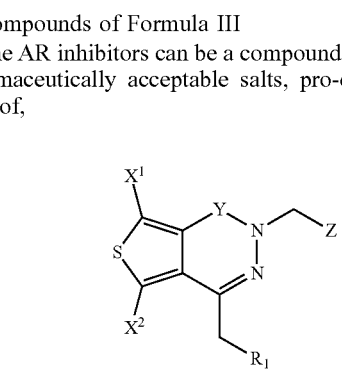

Compounds of Formula III

The AR inhibitors can be a compound of Formula (III) or pharmaceutically acceptable salts, pro-drugs and solvates thereof,

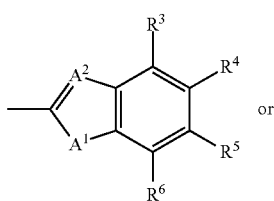

(III)

wherein, $R^1$ is $CO_2R^2$ or $CO_2^-X^+$;

$R^2$ is H, $(C_1-C_6)$-alkyl, $(C_1-C_6)$-hydroxyalkyl, or $(C_1-C_6)$-aminoalkyl;

$X^1$ is H or halogen;

$X^2$ is H or halogen;

Y is a bond, C=O, C=S, C=NH, or C=N($C_1-C_4$)-alkyl;

Z is

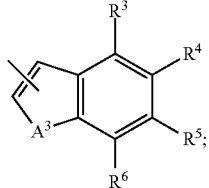

or

-continued

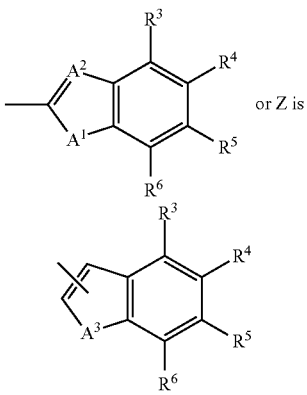

$A^1$ is $NR^7$, O, S or $CH_2$;

$A^2$ is N or CH;

$A^3$ is $NR^7$, O, or S;

$R^3$ through $R^6$ are independently hydrogen, halogen, cyano, acyl, haloalkyl, haloalkoxy, haloalkylthio, trifluoroacetyl, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkylsulfonyl;

$R^7$ is hydrogen, $C_1-C_4$ alkyl, or C(O)O—$(C_1-C_4)$-alkyl; and $X^+$ is a counter ion.

It will be recognized by those of skill in the art that the designation of

Z is

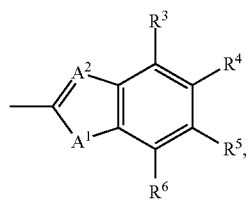

indicates that when Z is

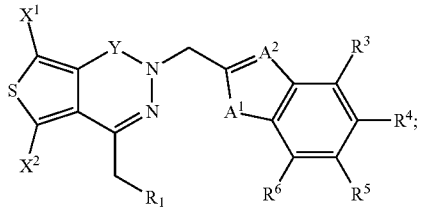

the compounds of Formula (III) are understood to encompass (III-1)

and when Z is the compounds of Formula (I) are understood to encompass (III-2)

(III-3)

In certain embodiments, $R^1$ is $CO_2R^2$ or $CO_2^-X^+$. In certain embodiments, $R^1$ is $CO_2R^2$. In certain embodiments, $R^1$ is $CO_2^-X^+$.

In certain embodiments, $R^2$ is hydrogen or $(C_1$-$C_6)$-alkyl. In certain embodiments, $R^2$ is hydrogen or $(C_1$-$C_4)$-alkyl. In certain embodiments, $R^2$ is hydrogen or $(C_1$-$C_3)$-alkyl. In certain embodiments, $R^2$ is hydrogen, methyl, or ethyl. In certain embodiments, $R^2$ is hydrogen or methyl. In certain embodiments, $R^2$ is methyl or ethyl. In certain embodiments, $R^2$ is methyl. In certain embodiments, $R^2$ is hydrogen. In certain embodiments, $R^2$ is $(C_1$-$C_6)$-alkyl. In certain embodiments, $R^2$ is $(C_1$-$C_6)$-n-alkyl. In certain embodiments, $R^2$ is $(C_1$-$C_2)$-alkyl. In certain embodiments, $R^2$ is $(C_1$-$C_3)$-alkyl. In certain embodiments, $R^2$ is $(C_1$-$C_4)$-alkyl. In certain embodiments, $R^2$ is tert-butyl.

In certain embodiments, $R^3$ through $R^6$ are independently hydrogen, halogen, cyano, acyl, haloalkyl, haloalkoxy, haloalkylthio, trifluoroacetyl, $(C_1$-$C_4)$-alkyl, $(C_1$-$C_4)$-alkoxy, $(C_1$-$C_4)$-alkylthio, $(C_1$-$C_4)$-alkylsulfinyl, or $(C_1$-$C_4)$-alkylsulfonyl.

In certain embodiments, $R^3$ through $R^6$ are independently hydrogen, halogen or haloalkyl. In certain embodiments, $R^3$ through $R^6$ are independently hydrogen, halogen or trihaloalkyl.

In certain embodiments, $R^3$ and $R^6$ are hydrogen. In certain embodiments, $R^3$, $R^5$, and $R^6$ are hydrogen.

In certain embodiments, $R^4$ is hydrogen, halogen or haloalkyl. In certain embodiments, $R^4$ is hydrogen. In certain embodiments, $R^4$ is halogen. In certain embodiments, $R^4$ is haloalkyl. In certain embodiments, $R^4$ is $CF_3$.

In certain embodiments, $R^3$ through $R^6$ are hydrogen. In certain embodiments, $R^3$, $R^5$, $R^6$ are hydrogen and $R^4$ is halogen or haloalkyl. In certain embodiments, $R^3$, $R^5$, $R^6$ are hydrogen and $R^4$ is haloalkyl. In certain embodiments, $R^3$, $R^5$, $R^6$ are hydrogen and $R^4$ is $CF_3$. In certain embodiments, $R^3$, $R^5$, $R^6$ are hydrogen and $R^4$ is halogen. In certain embodiments, $R^3$, $R^5$, $R^6$ are hydrogen and $R^4$ is F. In certain embodiments, $R^3$, $R^5$, $R^6$ are hydrogen and $R^4$ is Cl.

In certain embodiments, Y is C=O, C=S, C=NH, or C=N$(C_1$-$C_4)$-alkyl. In certain embodiments, Y is C=O or C=S. In certain embodiments, Y is C=O. In certain embodiments, Y is C=S. In certain embodiments, Y is C=NH, or C=N$(C_1$-$C_4)$-alkyl.

In certain embodiments, $A^1$ is $NR^7$, O, S or $CH_2$. In certain embodiments, $A^1$ is $NR^7$, O, or S. In certain embodiments, $A^1$ is $NR^7$, S or $CH_2$. In certain embodiments, $A^1$ is $NR^7$ or O. In certain embodiments, $A^1$ is $NR^7$ or S. In certain embodiments, $A^1$ is $NR^7$. In certain embodiments, $A^1$ is O. In certain embodiments, $A^1$ is S.

In certain embodiments, $A^2$ is N or CH. In certain embodiments, $A^2$ is N. In certain embodiments, $A^2$ is CH.

In certain embodiments, $A^3$ is $NR^7$, O, or S. In certain embodiments, $A^3$ is O. In certain embodiments, $A^3$ is S. In certain embodiments, $A^3$ is $NR^7$.

In certain embodiments, $X^1$ and $X^2$ are hydrogen.

In certain embodiments, $X^1$ and $X^2$ are halogen. In certain embodiments, $X^1$ and $X^2$ are Cl.

In certain embodiments, $X^1$ and $X^2$ are independently hydrogen or halogen. In certain embodiments, $X^1$ is hydrogen and $X^2$ is Cl. In certain embodiments, $X^1$ is Cl and $X^2$ is hydrogen.

In certain embodiments, Z is

In certain embodiments, Z is

In certain embodiments, $R^7$ is hydrogen, $C_1$-$C_4$ alkyl, or C(O)O—$(C_1$-$C_4)$-alkyl. In certain embodiments, $R^7$ is hydrogen. In certain embodiments, $R^7$ is $C_1$-$C_4$ alkyl. In certain embodiments, $R^7$ is $C_1$-$C_3$ alkyl. In certain embodiments, $R^7$ is $C_1$-$C_2$ alkyl. In certain embodiments, $R^7$ is $C_1$-$C_4$ n-alkyl. In certain embodiments, $R^7$ is $C_1$-$C_3$ n-alkyl. In certain embodiments, $R^7$ is C(O)O—$(C_1$-$C_4)$-alkyl. In certain embodiments, $R^7$ is C(O)O—$(C_1$-$C_3)$-alkyl. In certain embodiments, $R^7$ is C(O)O—$(C_1$-$C_2)$-alkyl. In certain embodiments, $R^7$ is C(O)O—$(C_1$-$C_4)$-n-alkyl. In certain embodiments, $R^7$ is C(O)O—$(C_1$-$C_3)$-n-alkyl.

In certain embodiments, $R^1$ is $CO_2R^2$;
$R^2$ is H or $(C_1$-$C_6)$-alkyl;
$X^1$ is H;
$X^2$ is H;
Y is C=O;

Z is

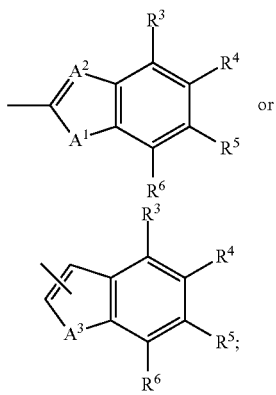 or

A¹ is NR⁷, O, or S;
A² is N;
A³ is O or S;
R³ through R⁶ are independently hydrogen, halogen, cyano, acyl, haloalkyl, haloalkoxy, haloalkylthio, trifluoroacetyl, $(C_1\text{-}C_4)$-alkyl, $(C_1\text{-}C_4)$-alkoxy, $(C_1\text{-}C_4)$-alkylthio, $(C_1\text{-}C_4)$-alkylsulfinyl, or $(C_1\text{-}C_4)$-alkylsulfonyl; and
R⁷ is hydrogen, $C_1\text{-}C_4$ alkyl, or C(O)O—$(C_1\text{-}C_4)$-alkyl.
In certain embodiments, R¹ is $CO_2R^2$;
R² is H or tert-butyl;
X¹ is H;
X² is H;
Y is C=O;
Z is

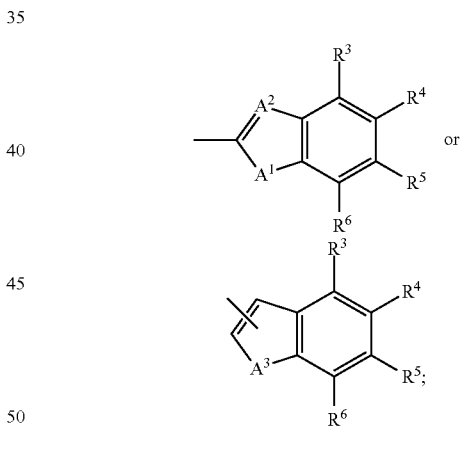 or

A¹ is NR⁷, O, or S;
A² is N;
A³ is O or S;
R⁶ through R⁶ are independently hydrogen, halogen, haloalkyl; and
R⁷ is hydrogen, $C_1\text{-}C_4$ alkyl, or C(O)O—$(C_1\text{-}C_4)$-alkyl.
In certain embodiments, R¹ is $CO_2R^2$;
R² is H or tert-butyl;
X¹ is H;
X² is H;
Y is C=O;

Z is

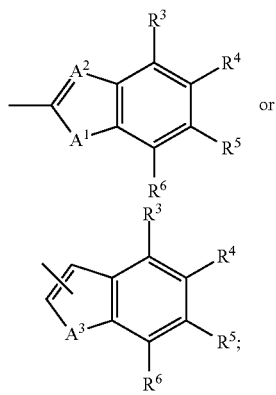 or

A¹ is NR⁷, O, or S;
A² is N;
A³ is O or S;
R³, R⁵, and R⁶ are hydrogen;
R⁴ is hydrogen, halogen, or haloalkyl; and
R⁷ is hydrogen, $C_1\text{-}C_4$ alkyl, or C(O)O—$(C_1\text{-}C_4)$-alkyl.
In certain embodiments, R¹ is $CO_2R^2$;
R² is H or $(C_1\text{-}C_6)$-alkyl;
X¹ is halogen;
X² is halogen;
Y is C=O;
Z is A¹ is NR⁷, O, or S;
A² is N;
A³ is O or S;
R³ through R⁶ are independently hydrogen, halogen, cyano, acyl, haloalkyl, haloalkoxy, haloalkylthio, trifluoroacetyl, $(C_1\text{-}C_4)$-alkyl, $(C_1\text{-}C_4)$-alkoxy, $(C_1\text{-}C_4)$-alkylthio, $(C_1\text{-}C_4)$-alkylsulfinyl, or $(C_1\text{-}C_4)$-alkylsulfonyl; and
R⁷ is hydrogen, $C_1\text{-}C_4$ alkyl, or C(O)O—$(C_1\text{-}C_4)$-alkyl.
In certain embodiments, R¹ is $CO_2R^2$;
R² is H or tert-butyl;
X¹ is halogen;
X² is halogen;
Y is C=O;

Z is

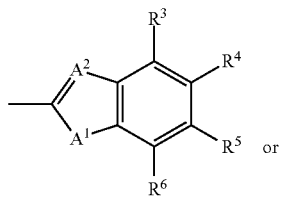

$A^1$ is $NR^7$, O, or S;
$A^2$ is N;
$A^3$ is O or S;
$R^3$ through $R^6$ are independently hydrogen, halogen, haloalkyl; and
$R^7$ is hydrogen, $C_1$-$C_4$ alkyl, or C(O)O—($C_1$-$C_4$)-alkyl.

In certain embodiments, $R^1$ is $CO_2R^2$;
$R^2$ is H or tert-butyl;
$X^1$ is Cl;
$X^2$ is Cl;
Y is C=O;
Z is

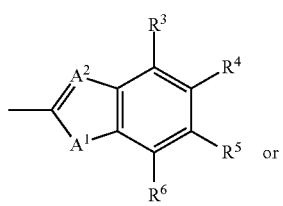

$A^1$ is $NR^7$, O, or S;
$A^2$ is N;
$A^3$ is O or S;
$R^3$ through $R^6$ are independently hydrogen, halogen, haloalkyl; and
$R^7$ is hydrogen, $C_1$-$C_4$ alkyl, or C(O)O—($C_1$-$C_4$)-alkyl.

In certain embodiments, $R^1$ is $CO_2R^2$;
$R^2$ is H or tert-butyl;
$X^1$ is Cl;
$X^2$ is Cl;
Y is C=O;
Z is

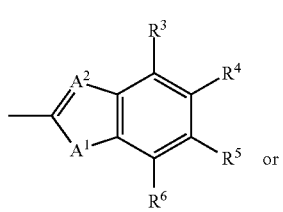

$A^1$ is $NR^7$, O, or S;
$A^2$ is N;
$A^3$ is O or S;
$R^3$, $R^5$, and $R^6$ are hydrogen;
$R^4$ is hydrogen, halogen, or haloalkyl; and
$R^7$ is hydrogen, $C_1$-$C_4$ alkyl, or C(O)O—($C_1$-$C_4$)-alkyl.

In certain embodiments, the compound of Formula (III) is selected from the group consisting of:

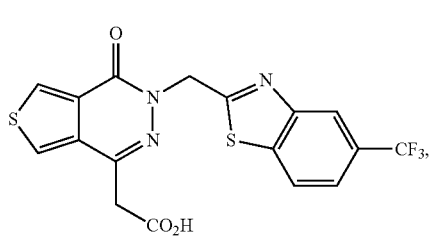

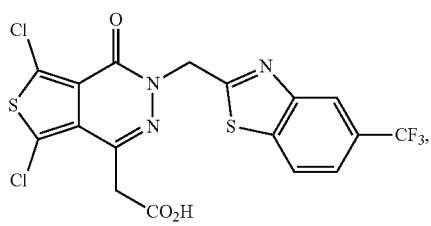

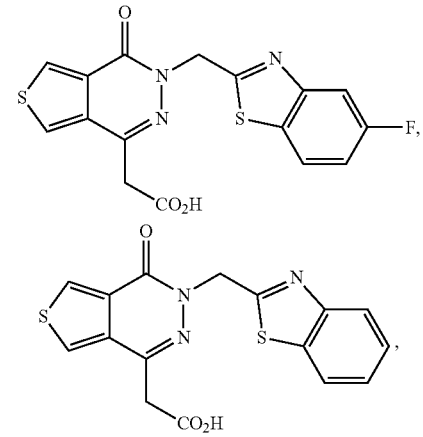

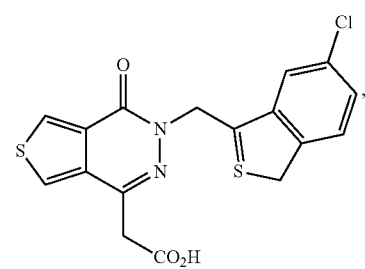

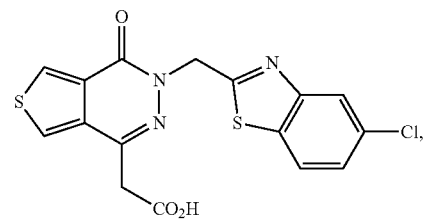 [SMILES: O=C(O)Cc1nn(Cc2cc3cc(Cl)ccc3o2)c(=O)c2cscc12]

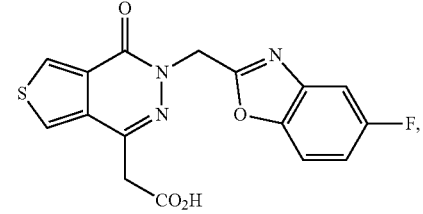

-continued

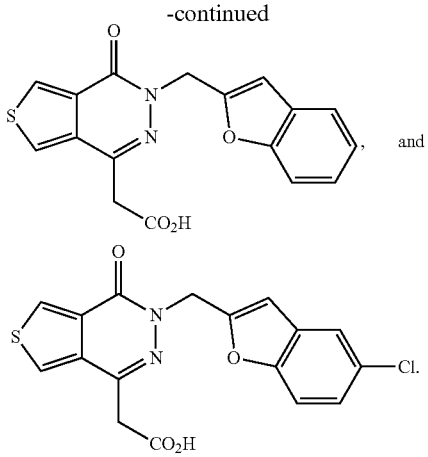

and

In certain embodiments, the compound of Formula (I) is

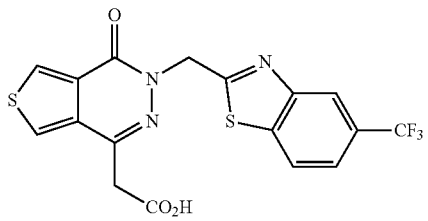 [SMILES: O=C(O)Cc1nn(Cc2nc3cc(C(F)(F)F)ccc3s2)c(=O)c2cscc12]

or a pharmaceutically acceptable salt thereof.

In certain embodiments, the compound of formula (I) is

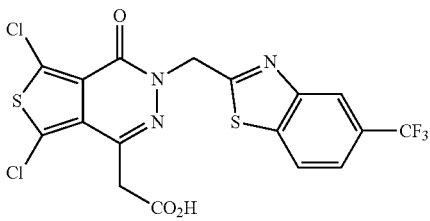 [SMILES: O=C(O)Cc1nn(Cc2nc3cc(C(F)(F)F)ccc3s2)c(=O)c2c(Cl)sc(Cl)c12]

or a pharmaceutically acceptable salt thereof.

Compounds of Formulas IV, V and VI

The AR inhibitors can be a compound of Formula (IV) or pharmaceutically acceptable salts, and solvates thereof,

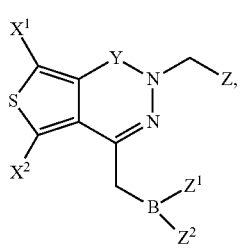
(IV)

wherein,
$X^1$ is H or halogen;
$X^2$ is H or halogen;
Y is a bond, C=O, C=S, C=NH, or C=N($C_1$-$C_4$)-alkyl;
$Z^1$ and $Z^2$ are independently selected from the group consisting of hydroxy, alkoxy, aryloxy, or $Z^1$ and $Z^2$ taken together with the boron atom to which they are bonded form

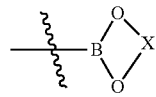

wherein,
X is a substituted or unsubstituted $C_2$-$C_5$ alkylene;
Z is

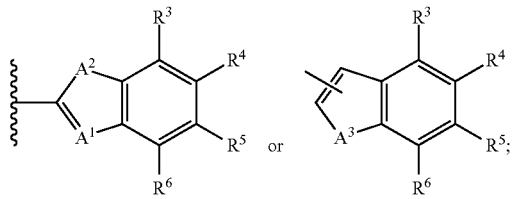

$A^1$ is $NR^7$, O, S or $CH_2$;
$A^2$ is N or CH;
$A^3$ is $NR^7$, O, or S;
$R^3$ through $R^6$ are independently hydrogen, halogen, cyano, acyl, haloalkyl, haloalkoxy, haloalkylthio, trifluoroacetyl, ($C_1$-$C_4$)-alkyl, ($C_1$-$C_4$)-alkoxy, ($C_1$-$C_4$)-alkylthio, ($C_1$-$C_4$)-alkylsulfinyl, or ($C_1$-$C_4$)-alkylsulfonyl; and
$R^7$ is hydrogen, $C_1$-$C_4$ alkyl, or C(O)O—($C_1$-$C_4$)-alkyl.

Suitable substituents on the $C_2$-$C_5$ alkylene include one or more alkyl, alkoxy, aryl, aryloxy, halo, haloalkyl, haloalkoxy, haloalkylthio. A preferred substituted $C_2$-$C_5$ alkylene is substituted ethylene. A more preferred substituted $C_2$-$C_5$ alkylene is —C($CH_3$)$_2$C($CH_3$)$_2$—.

It will be recognized by those of skill in the art that the designation of
Z is

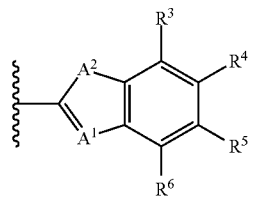

or Z is

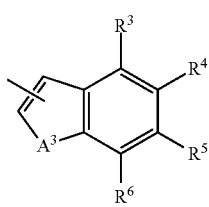

indicates that when Z is

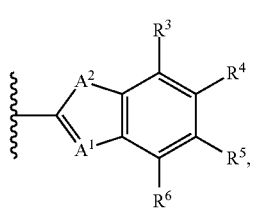

the compounds of Formula (IV) are understood to encompass

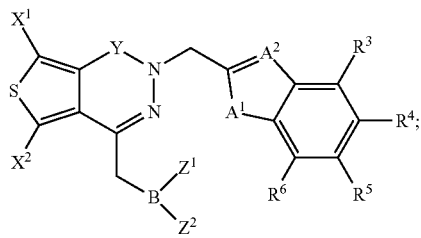
(IVa)

and
when Z is

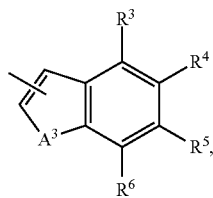

the compounds of Formula (IV) are understood to encompass

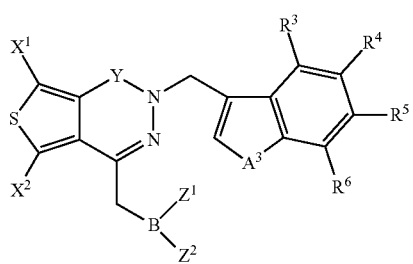
(IVb)

and

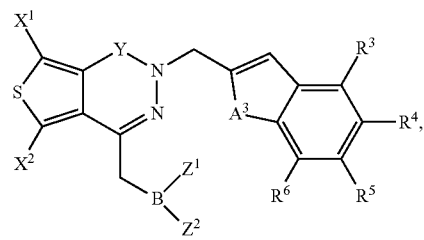
(IVc)

wherein, $Z^1$ and $Z^2$ are independently selected from the group consisting of hydroxy, alkoxy, aryloxy, or $Z^1$ and $Z^2$ taken together with the boron atom to which they are bonded form

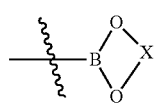

wherein,

X is a substituted or unsubstituted $C_2$-$C_5$ alkylene.

In certain embodiments, $R^3$ through $R^6$ of Formula (IV) are independently hydrogen, halogen, cyano, acyl, haloalkyl, haloalkoxy, haloalkylthio, trifluoroacetyl, $(C_1$-$C_4)$-alkyl, $(C_1$-$C_4)$-alkoxy, $(C_1$-$C_4)$-alkylthio, $(C_1$-$C_4)$-alkylsulfinyl, or $(C_1$-$C_4)$-alkylsulfonyl.

In certain embodiments, $R^3$ through $R^6$ of Formula (IV) are independently hydrogen, halogen or haloalkyl. In certain embodiments, $R^3$ through $R^6$ are independently hydrogen, halogen or trihaloalkyl.

In certain embodiments, $R^3$ and $R^6$ of Formula (IV) are hydrogen. In certain embodiments, $R^3$, $R^5$, and $R^6$ are hydrogen.

In certain embodiments, $R^4$ of Formula (IV) is hydrogen, halogen or haloalkyl. In certain embodiments, $R^4$ is hydrogen. In certain embodiments, $R^4$ is halogen. In certain embodiments, $R^4$ is haloalkyl. In certain embodiments, $R^4$ is $CF_3$.

In certain embodiments, $R^3$ through $R^6$ of Formula (IV) are hydrogen. In certain embodiments, $R^3$, $R^5$, $R^6$ are hydrogen and $R^4$ is halogen or haloalkyl. In certain embodiments, $R^3$, $R^5$, $R^6$ are hydrogen and $R^4$ is haloalkyl. In certain embodiments, $R^3$, $R^5$, $R^6$ are hydrogen and $R^4$ is $CF_3$. In certain embodiments, $R^3$, $R^5$, $R^6$ are hydrogen and $R^4$ is halogen. In certain embodiments, $R^3$, $R^5$, $R^6$ are hydrogen and $R^4$ is F. In certain embodiments, $R^3$, $R^5$, $R^6$ are hydrogen and $R^4$ is Cl.

In certain embodiments, Y of Formula (IV) is C=O, C=S, C=NH, or C=N($C_1$-$C_4$)-alkyl. In certain embodiments, Y is C=O or C=S. In certain embodiments, Y is C=O. In certain embodiments, Y is C=S. In certain embodiments, Y is C=NH, or C=N($C_1$-$C_4$)-alkyl.

In certain embodiments, $A^1$ of Formula (IV) is $NR^7$, O, S or $CH_2$. In certain embodiments, $A^1$ is $NR^7$, O, or S. In certain embodiments, $A^1$ is $NR^7$, S or $CH_2$. In certain embodiments, $A^1$ is $NR^7$ or O. In certain embodiments, $A^1$ is $NR^7$ or S. In certain embodiments, $A^1$ is $NR^7$. In certain embodiments, $A^1$ is O. In certain embodiments, $A^1$ is S.

In certain embodiments, $A^2$ of Formula (IV) is N or CH. In certain embodiments, $A^2$ is N. In certain embodiments, $A^2$ is CH.

In certain embodiments, $A^3$ of Formula (IV) is $NR^7$, O, or S. In certain embodiments, $A^3$ is O. In certain embodiments, $A^3$ of Formula (IV) is S. In certain embodiments, $A^3$ is $NR^7$.

In certain embodiments, $X^1$ and $X^2$ of Formula (IV) are hydrogen.

In certain embodiments, $X^1$ and $X^2$ of Formula (IV) are halogen. In certain embodiments, $X^1$ and $X^2$ are Cl.

In certain embodiments, $X^1$ and $X^2$ of Formula (IV) are independently hydrogen or halogen. In certain embodiments, $X^1$ is hydrogen and $X^2$ is Cl. In certain embodiments, $X^1$ is Cl and $X^2$ is hydrogen.

In certain embodiments, Z of Formula (IV) is

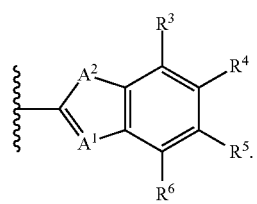

In certain embodiments, Z of Formula (IV) is

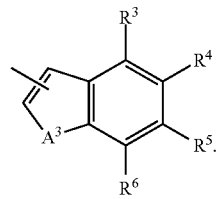

In certain embodiments, $R^7$ of Formula (IV) is hydrogen, $C_1$-$C_4$ alkyl, or C(O)O—($C_1$-$C_4$)-alkyl. In certain embodiments, $R^7$ is hydrogen. In certain embodiments, $R^7$ is $C_1$-$C_4$ alkyl. In certain embodiments, $R^7$ is $C_1$-$C_3$ alkyl. In certain embodiments, $R^7$ is $C_1$-$C_2$ alkyl. In certain embodiments, $R^7$ is $C_1$-$C_4$ n-alkyl. In certain embodiments, $R^7$ is $C_1$-$C_3$ n-alkyl. In certain embodiments, $R^7$ is C(O)O—($C_1$-$C_4$)-alkyl. In certain embodiments, $R^7$ is C(O)O—($C_1$-$C_3$)-alkyl. In certain embodiments, $R^7$ is C(O)O—($C_1$-$C_2$)-alkyl. In certain embodiments, $R^7$ is C(O)O—($C_1$-$C_4$)-n-alkyl. In certain embodiments, $R^7$ is C(O)O—($C_1$-$C_3$)-n-alkyl.

In certain embodiments, the compounds of Formula (IV) is

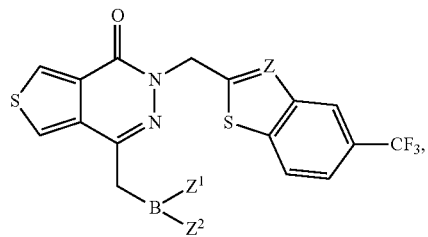

or pharmaceutically acceptable salts, pro-drugs or solvates thereof;

wherein, $Z^1$ and $Z^2$ are independently selected from the group consisting of hydroxy, alkoxy, aryloxy, or $Z^1$ and $Z^2$ taken together with the boron atom to which they are bonded form

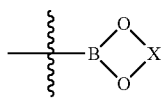

wherein,

X is a substituted or unsubstituted $C_2$-$C_5$ alkylene.

In certain embodiments, the compounds of Formula (IV) is

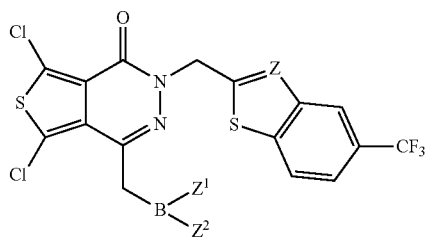

or pharmaceutically acceptable salts, pro-drugs or solvates thereof;

wherein, $Z^1$ and $Z^2$ are independently selected from the group consisting of hydroxy, alkoxy, aryloxy, or $Z^1$ and $Z^2$ taken together with the boron atom to which they are bonded form

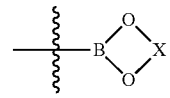

wherein,

X is a substituted or unsubstituted $C_2$-$C_5$ alkylene.

In certain embodiments, the compounds of Formula (IV) is

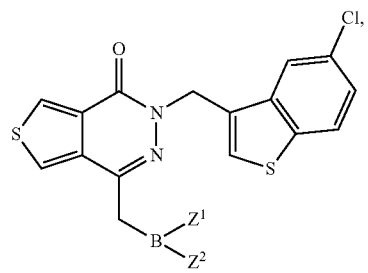

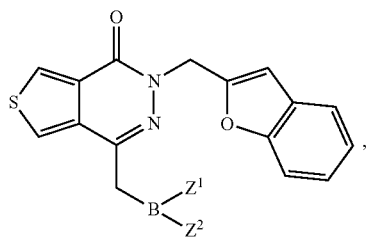

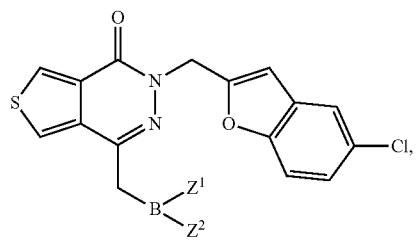

or pharmaceutically acceptable salts, pro-drugs or solvates thereof;

wherein, $Z^1$ and $Z^2$ are independently selected from the group consisting of hydroxy, alkoxy, aryloxy, or $Z^1$ and $Z^2$ taken together with the boron atom to which they are bonded form

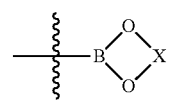

wherein,

X is a substituted or unsubstituted $C_2$-$C_5$ alkylene.

In certain embodiments, the compounds of Formula (IV) is

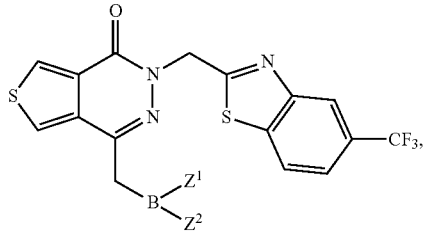

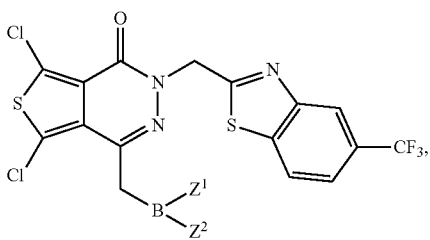

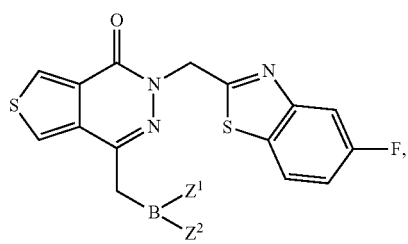

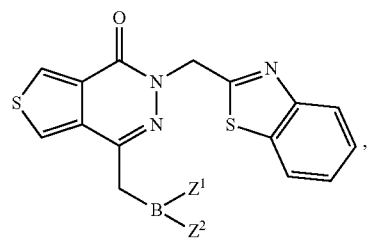

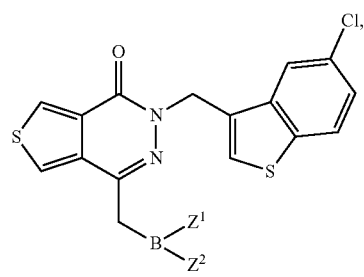

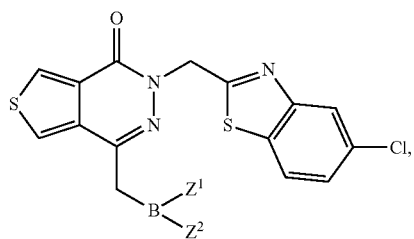

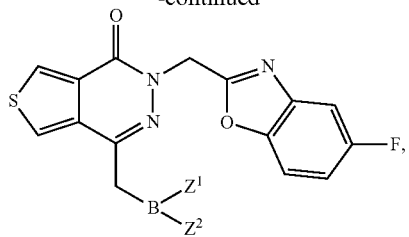

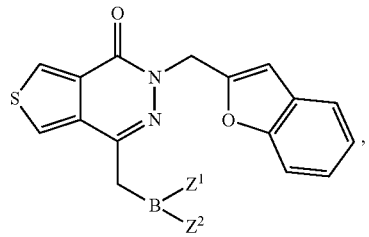

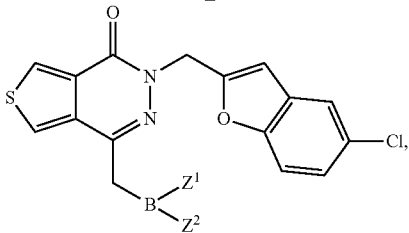

or pharmaceutically acceptable salts, pro-drugs or solvates thereof;

wherein, $Z^1$ and $Z^2$ are independently selected from the group consisting of hydroxy, alkoxy, aryloxy, or $Z^1$ and $Z^2$ taken together with the boron atom to which they are bonded form

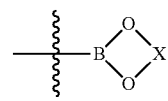

wherein,

X is a substituted or unsubstituted $C_2$-$C_5$ alkylene.

In another aspect, the aldose reductase inhibitor is a compound of Formula (V)

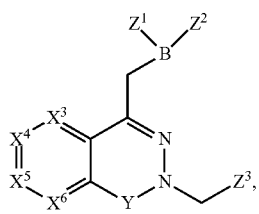

(V)

or pharmaceutically acceptable salts, pro-drugs or solvates thereof;

wherein, $X^3$ is N or $CR^8$;

$X^4$ is N or $CR^9$;

$X^5$ is N or $CR^{10}$;

$X^6$ is N or $CR^{11}$; with the proviso that two or three of $X^3$, $X^4$, $X^5$, or $X^6$ are N;

$Z^1$ and $Z^2$ are independently selected from the group consisting of hydroxy, alkoxy, aryloxy, or $Z^1$ and $Z^2$ taken together with the boron atom to which they are bonded form

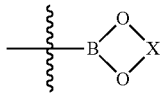

wherein,
X is a substituted or unsubstituted $C_2$-$C_5$ alkylene;
$Z^3$ is

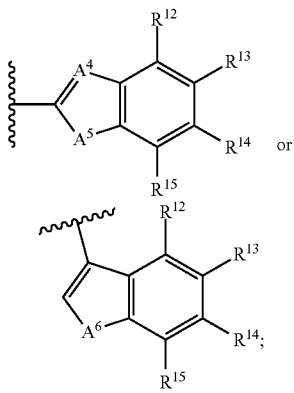

$A^4$ is $NR^{16}$, O, S or $CH_2$;
$A^5$ is N or CH;
$A^6$ is $NR^{16}$, O, or S;
$R^8$ through $R^{15}$ are independently hydrogen, halogen, cyano, acyl, haloalkyl, haloalkoxy, haloalkylthio, trifluoroacetyl, ($C_1$-$C_4$)-alkyl, ($C_1$-$C_4$)-alkoxy, ($C_1$-$C_4$)-alkylthio, ($C_1$-$C_4$)-alkylsulfinyl, or ($C_1$-$C_4$)-alkylsulfonyl; or two of $R^8$ through $R^{11}$ or two of $R^{12}$ through $R^{15}$ taken together are ($C_1$-$C_4$)-alkylenedioxy; and
$R^{16}$ is hydrogen, $C_1$-$C_4$ alkyl, or C(O)O—($C_1$-$C_4$)-alkyl.

Suitable substituents on the $C_2$-$C_5$ alkylene include one or more alkyl, alkoxy, aryl, aryloxy, halo, haloalkyl, haloalkoxy, haloalkylthio. A preferred substituted $C_2$-$C_5$ alkylene is substituted ethylene. A more preferred substituted $C_2$-$C_5$ alkylene is —C(CH$_3$)$_2$C(CH$_3$)$_2$—.

It will be recognized by those of skill in the art that the designation of
Z is

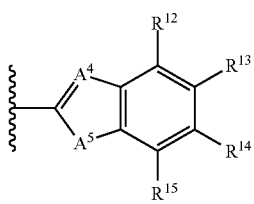

or Z is

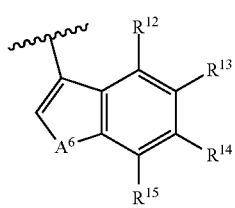

indicates that when Z is

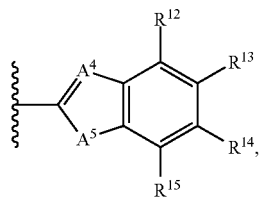

the compounds of Formula (V) are understood to encompass (Va)

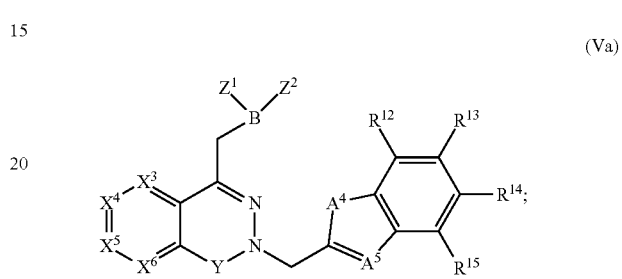

and when Z is

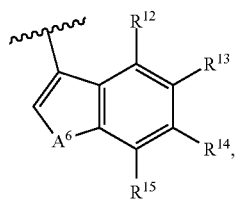

the compounds of Formula (V) are understood to encompass (Vb)

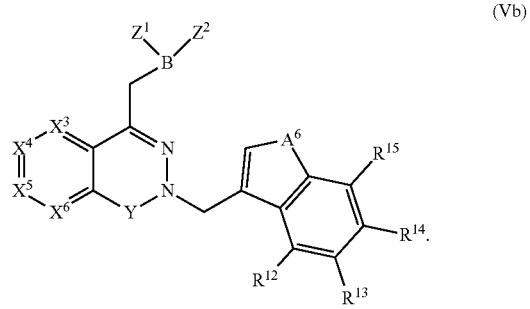

In some compounds of Formula V, $R^8$ through $R^{15}$ are independently hydrogen, halogen or haloalkyl, for example, $R^8$ through $R^{15}$ are independently hydrogen, halogen or trihaloalkyl (e.g., —CF$_3$).

In other compounds of Formula V, $R^8$ through $R^{11}$ are hydrogen.

In certain embodiments of compounds of Formula V, $R^{12}$ through $R^{15}$ are independently hydrogen, halogen or haloalkyl, for example, $R^{12}$ through $R^{15}$ are independently hydrogen, halogen or trihaloalkyl (e.g., —CF$_3$).

In certain embodiments, $R^{12}$ and $R^{15}$ of Formula (V) are hydrogen.

In certain embodiments, $R^{13}$ of Formula (V) is hydrogen, halogen or haloalkyl. In certain embodiments, $R^{13}$ is hydrogen. In certain embodiments, $R^{13}$ is halogen. In certain embodiments, $R^{13}$ is haloalkyl.

In certain embodiments, $R^{14}$ of Formula (V) is hydrogen, halogen or haloalkyl. In certain embodiments, $R^{14}$ is hydrogen. In certain embodiments, $R^{14}$ is halogen. In certain embodiments, $R^{14}$ is haloalkyl.

In certain embodiments, Y of Formula (V) is C=O, C=S, C=NH, or C=N($C_1$-$C_4$)-alkyl. In certain embodiments, Y is C=O or C=S. In certain embodiments, Y is C=O. In certain embodiments, Y is C=S. In certain embodiments, Y is C=NH, or C=N($C_1$-$C_4$)-alkyl.

In certain embodiments, $A^4$ of Formula (V) is $NR^{16}$, S or $CH_2$. In certain embodiments, $A^4$ is $NR^{16}$ or O. In certain embodiments, $A^4$ is $NR^{16}$ or S. In certain embodiments, $A^4$ is $NR^{16}$. In certain embodiments, $A^4$ is O. In certain embodiments, $A^4$ is S.

In certain embodiments, $A^5$ of Formula (V) is N or CH. In certain embodiments, $A^4$ is N. In certain embodiments, $A^4$ is CH.

In certain embodiments, $A^6$ of Formula (V) is O or S. In certain embodiments, $A^6$ is O. In certain embodiments, $A^6$ is S.

In certain embodiments, $X^3$ and $X^6$ of Formula (V) are nitrogen.

In certain embodiments, $X^3$ and $X^4$ of Formula (V) are nitrogen.

In certain embodiments, $X^3$ and $X^5$ of Formula (V) are nitrogen.

In certain embodiments, $X^4$ and $X^5$ of Formula (V) are nitrogen.

In certain embodiments, $X^4$ and $X^6$ of Formula (V) are nitrogen.

In certain embodiments, $X^5$ and $X^6$ of Formula (V) are nitrogen.

In certain embodiments, $Z^3$ of Formula (V) is

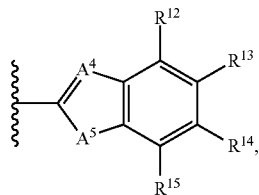

In certain embodiments, $Z^3$ of Formula (V) is

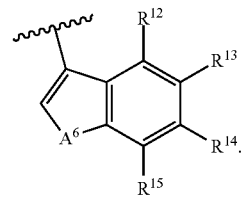

In some embodiments, the compounds of Formula (V) is

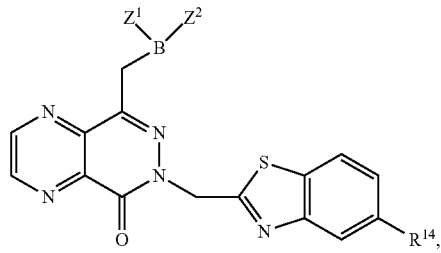

or pharmaceutically acceptable salts, pro-drugs or solvates thereof;

wherein, $R^{14}$ is hydrogen, halogen or trihaloalkyl (e.g., —$CF_3$); and $Z^1$ and $Z^2$ are independently selected from the group consisting of hydroxy, alkoxy, aryloxy, or $Z^1$ and $Z^2$ taken together with the boron atom to which they are bonded form

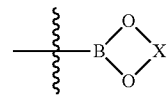

wherein,

X is a substituted or unsubstituted $C_2$-$C_5$ alkylene.

In embodiments, the compounds of Formula (V) is

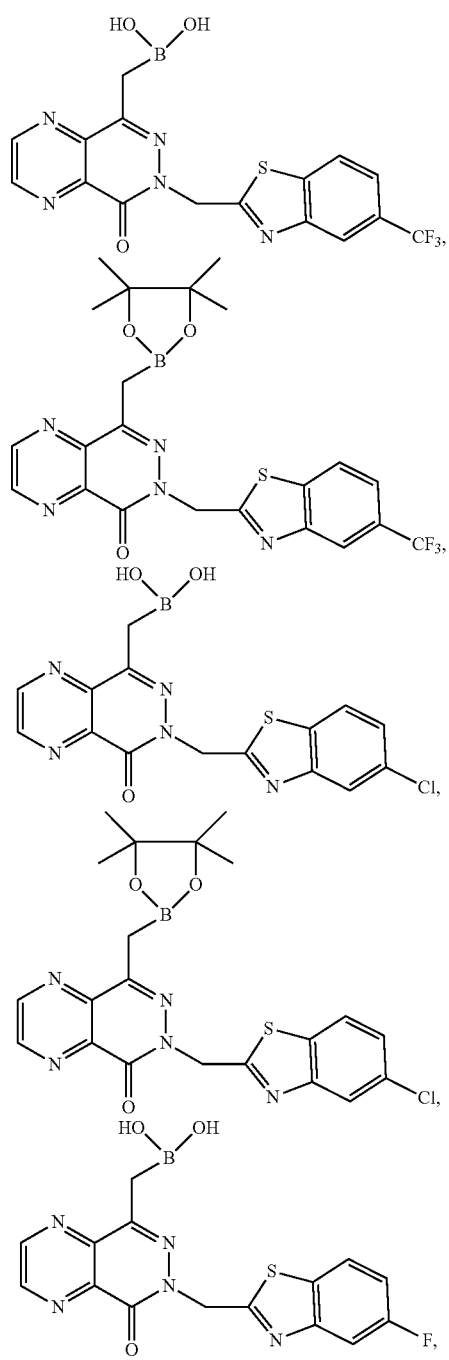

-continued

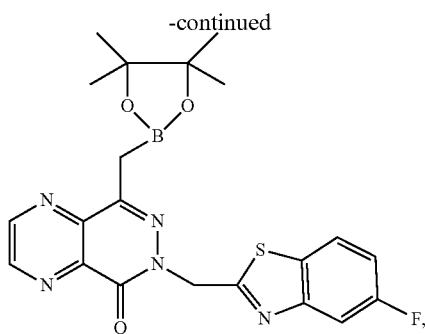

or pharmaceutically acceptable salts, pro-drugs or solvates thereof.

In one aspect, the aldose reductase inhibitor is a compound of Formula (VI)

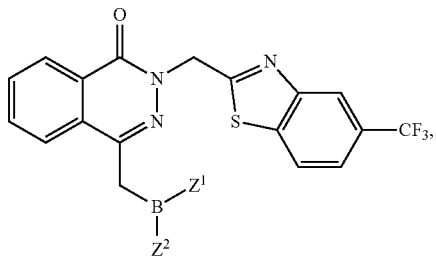

(VI)

or pharmaceutically acceptable salts, pro-drugs or solvates thereof;

wherein, $Z^1$ and $Z^2$ are independently selected from the group consisting of hydroxy, alkoxy, aryloxy, or $Z^1$ and $Z^2$ taken together with the boron atom to which they are bonded form

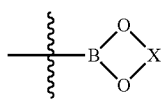

wherein,

X is a substituted or unsubstituted $C_2$-$C_5$ alkylene.

In an embodiment, the aldose reductase inhibitor of Formula (VI) is

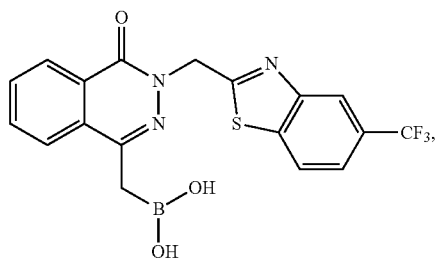 [SMILES: O=c1c2ccccc2c(CB(O)O)nn1Cc1nc2cc(C(F)(F)F)ccc2s1]

or pharmaceutically acceptable salts, pro-drugs or solvates thereof.

In an embodiment, the AH inhibitor of Formula (VI) is

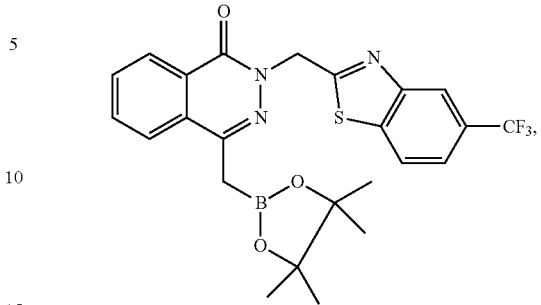

or pharmaceutically acceptable salts, pro-drugs or solvates thereof.

The term "alkyl", as used herein, unless otherwise indicated, refers to a monovalent aliphatic hydrocarbon radical having a straight chain, branched chain, monocyclic moiety, or polycyclic moiety or combinations thereof, wherein the radical is optionally substituted at one or more carbons of the straight chain, branched chain, monocyclic moiety, or polycyclic moiety or combinations thereof with one or more substituents at each carbon, where the one or more substituents are independently $C_1$-$C_{10}$ alkyl. Examples of "alkyl" groups include methyl, ethyl, propyl, isopropyl, butyl, isobutyl, sec-butyl, tert-butyl, pentyl, hexyl, heptyl, cyclopropyl, cyclobutyl, cyclopentyl, cyclohexyl, cycloheptyl, norbornyl, and the like.

The term "halogen" or "halo-", as used herein, means chlorine (Cl), fluorine (F), iodine (I) or bromine (Br).

As used herein, the term "acyl" is used in a broad sense to designate radicals of the type RCO—, in which R represents an organic radical which may be an alkyl, aralkyl, aryl, alicyclic or heterocyclic radical, substituted or unsubstituted, saturated or unsaturated; or, differently defined, the term "acyl" is used to designate broadly the monovalent radicals left when the OH group of the carboxylic radical is removed from the molecule of a carboxylic acid.

The term "alkoxy" is employed to designate a group of the formula: —O—R wherein R is an alkyl group, which optionally contains substituents, such as halogen. Preferably, the term "alkoxy" is employed to designate an alkoxy with an alkyl group of 1 to 6 carbon atoms. Most preferably, the term "alkoxy" is employed to designate an alkoxy with an alkyl group of 1 to 3 carbon atoms, such as methoxy or ethoxy.

The term "cycloalkyl group" is used herein to identify cycloalkyl groups having 3-6 carbon atoms preferably cyclopropyl, cyclobutyl, cyclopentyl and cyclohexyl.

The term "solvate" as used herein means a compound, or a pharmaceutically acceptable salt thereof, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

A "prodrug" refers to an agent, which is converted into the parent drug in vivo. Prodrugs are often useful because, in some situations, they are easier to administer than the parent drug. They are bioavailable, for instance, by oral administration whereas the parent drug is either less bioavailable or not bioavailable. The prodrug also has improved solubility in pharmaceutical compositions over the parent drug. For example, the compound carries protective groups which are split off by hydrolysis in body fluids, e.g., in the bloodstream, thus releasing active compound or is oxidized or reduced in body fluids to release the compound. The term "prodrug" may apply to such functionalities as, for example; the acid functionalities of the compounds of formula I. Prodrugs may be comprised of structures wherein an acid group is masked, for example, as an ester or amide. Further examples of prodrugs are discussed herein. See also Alexander et al. (*J. Med. Chem.* 1988, 31, 318), which is incorporated by reference. Examples of prodrugs include, but are not limited to, derivatives and metabolites of a compound that include biohydrolyzable moieties such as biohydrolyzable amides, biohydrolyzable esters, biohydrolyzable carbamates, biohydrolyzable carbonates, and biohydrolyzable phosphate analogues. Prodrugs are also described in, for example, *The Practice of Medicinal Chemistry* (Camille Wermuth, ed., 1999, Academic Press; hereby incorporated by reference in its entirety). In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* $6^{th}$ ed. (Donald J. Abraham ed., 2001, Wiley) and Design and *Application of Prodrugs* (H. Bundgaard ed., 1985, Harwood Academic Publishers Gmfh; each of which hereby incorporated by reference in its entirety). Biohydrolyzable moieties of a compound of Formula I (a) do not interfere with the biological activity of the compound but can confer upon that compound advantageous properties in vivo, such as uptake, duration of action, or onset of action; or (b) may be biologically inactive but are converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, amino acids, hydroxyalkylamines, heterocyclic and heteroaromatic amines, and polyether amines.

The term "salt" includes salts derived from any suitable of organic and inorganic counter ions well known in the art and include, by way of example, hydrochloric acid salt or a hydrobromic acid salt or an alkaline or an acidic salt of the aforementioned amino acids. The term is intended to include salts derived from inorganic or organic acids including, for example hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids; and salts derived from inorganic or organic bases including, for example sodium, potassium, calcium, ammonium or tetrafluoroborate. Exemplary pharmaceutically acceptable salts are found, for example, in Berge, et al. (*J. Pharm. Sci.* 1977, 66(1), 1; and U.S. Pat. Nos. 6,570,013 and 4,939,140; each hereby incorporated by reference in its entirety). Pharmaceutically acceptable salts are also intended to encompass hemi-salts, wherein the ratio of compound:acid is respectively 2:1. Exemplary hemi-salts are those salts derived from acids comprising two carboxylic acid groups, such as malic acid, fumaric acid, maleic acid, succinic acid, tartaric acid, glutaric acid, oxalic acid, adipic acid and citric acid. Other exemplary hemi-salts are those salts derived from diprotic mineral acids such as sulfuric acid. Exemplary preferred hemi-salts include, but are not limited to, hemimaleate, hemifumarate, and hemisuccinate.

The term "acid" contemplates all pharmaceutically acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically acceptable aliphatic, alicyclic and aromatic carboxylic acids, dicarboxylic acids, tricarboxylic acids, and fatty acids. Preferred acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, fumaric acid, acetic acid, propionic acid, isopropionic acid, valeric acid, alpha-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tartaric acid and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

III. Compositions

The compounds can be administered in the form a suitable composition, such as a pharmaceutical composition. Pharmaceutical compositions are physiologically acceptable and typically include the active compound and a carrier. The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in Remington's Pharmaceutical Sciences (Alfonso Gennaro ed., Krieger Publishing Company (1997); Remington's: The Science and Practice of Pharmacy, $21S^tEd.$ (Lippincot, Williams & Wilkins (2005); Modern Pharmaceutics, vol. 121 (Gilbert Banker and Christopher Rhodes, CRC Press (2002); each of which hereby incorporated by reference in its entirety). Particularly, the carrier can be suitable for ocular applications, e.g., application into the eye for the treatment of eye diseases, e.g., cataract. In another embodiment, the carrier may comprise a suppository for vaginal administration, e.g., for the treatment of premature ovarian insufficiency (POI).

The composition can be in a desired form, such as a table, capsule, solution, emulsion, suspension, gel, sol, or colloid that is physiologically and/or pharmaceutically acceptable. If desired, the carrier can include a buffer, for example with alkaline buffers, e.g., ammonium buffer, acidic buffers, e.g., ethanoates, citrates, lactates, acetates, etc., or zwitterionic buffers, such as, glycine, alanine, valine, leucine, isoleucine and phenylalanine, Kreb's-Ringer buffer, TRIS, MES, ADA, ACES, PIPES, MOPSO, cholamine chloride, MOPS, BES, TES, HEPES, DIPSO, MOBS, TAPSO, acetamidoglycine, TEA, POPSO, HEPPSO, EPS, HEPPS, Tricine, TRIZMA, Glycinamide, Glycyl-glycine, HEPBS, Bicine, TAPS, AMPB, CHES, AMP, AMPSO, CAPSO, CAPS, and CABS.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. If desired tonicity adjusting agents can be included, such as, for example, sugars, sodium chloride or combinations thereof. In some embodiments, the composition is isotonic.

The compositions may also include additional ingredients, such as acceptable surfactants, co-solvents, emollients, agents to adjust the pH and osmolarity and/or antioxidants to retard oxidation of one or more component.

The compositions can be prepared for administration by any suitable route such as ocular (including periocular and intravitreal administration), oral, parenteral, intranasal, anal, vaginal, topical, subcutaneous, intravenous, intra-arterial, intrathecal and intraperitoneal administration. As shown in the working examples disclosed herein, oral administration of aldose reductase inhibitors effectively lowered and normalized galactitol levels in blood and tissues, include brain. Accordingly, while intrathecal administration is an option and may be selected by a clinician (e.g., when the aldose reductase inhibitor is not central nervous system penetrant), it is generally preferred that the aldose reductase inhibitor is not administered intrathecally. For ocular administration, the composition may be formulated as, for example, drops, solutions, suspensions, emulsions, ointments, sustained release formulation, troche, elixir, syrup, wafer, powder or combinations thereof. See, Gaudana et al., *AAPS J.*, 12(3): 348-360, 2010. Oral compositions may be incorporated directly with the food of the diet. Preferred carriers for oral administration comprise inert diluents, edible carriers or combinations thereof. Examples of pharmaceutically acceptable carriers may include, for example, water or saline solution, polymers such as polyethylene glycol, carbohydrates and derivatives thereof, oils, fatty acids, or alcohols. Surfactants such as, for example, detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sulfate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula NR'R"R'"R""Y", in which the R radicals are identical or different optionally hydroxylated hydrocarbon radicals and Y" is an anion of a strong acid, such as halide, sulfate and sulfonate anions; cetyltrimethylammonium bromide is one of the cationic surfactants which can be used, amine salts of formula NR'R'R", in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine.

If desired, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc., or combinations thereof containing two or more of the foregoing.

Additional formulations which are suitable for other modes of administration include suppositories. Moreover, sterile injectable solutions may be prepared using an appropriate solvent. Generally, dispersions are prepared by incorporating the various sterilized amino acid components into a sterile vehicle, which contains the basic dispersion medium and/or the other ingredients. Suitable formulation methods for any desired mode of administration are well known in the art (see, generally, Remington's Pharmaceutical Sciences, 18$^{th}$ Ed. Mack Printing Company, 1990).

Typical pharmaceutically acceptable compositions can contain a an AR inhibitor and/or a pharmaceutically acceptable salt thereof at a concentration ranging from about 0.01 to about 2 wt %, such as 0.01 to about 1 wt % or about 0.05 to about 0.5 wt %. The composition can be formulated as a solution, suspension, ointment, or a capsule, and the like. The pharmaceutical composition can be prepared as an aqueous solution and can contain additional components, such as preservatives, buffers, tonicity agents, antioxidants, stabilizers, viscosity-modifying ingredients and the like. Other equivalent modes of administration can be found in U.S. Pat. No. 4,939,140.

When administered to a subject, the AR inhibitor and pharmaceutically acceptable carriers can be sterile. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical formulations of the present disclosure are prepared by methods well-known in pharmaceutics. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

In some embodiments, the composition is in unit dose form such as a tablet, capsule or single-dose vial. Suitable unit doses, i.e., therapeutically effective amounts, may be determined during clinical trials designed appropriately for each of the conditions for which administration of a chosen compound is indicated and will, of course, vary depending on the desired clinical endpoint.

Any of the compounds and/or compositions of the disclosure may be provided in a kit comprising the compounds and/or compositions. Thus, in one embodiment, the compound and/or composition of the disclosure is provided in a kit comprising in the same package or separate package, a carrier and optionally instructions for using the kit for therapeutic or prophylactic end usage.

IV. Combination therapy

The methods described herein include the administration of an AR inhibitor and one more additional therapeutic agents. The additional therapeutic agents may be administered before, concurrently with or after the AR inhibitor, but in a manner that provides for overlap of the pharmacological activity of the AR inhibitor and the additional therapeutic agent. The additional therapeutic agent can be, for example, second aldose reductase inhibitor, an antioxidant, or both.

For example, the $2^{nd}$ aldose reductase can be a compound described in, for example, U.S. Pat. Nos. 5,677,342; 5,155,259; 4,939,140; US US2006/0293265; and Roy et al. (*Diabetes Research and Clinical Practice*, 10, Issue 1, 91-97, 1990; and references cited therein; each of which hereby incorporated by reference in its entirety. Aldose reductase inhibitors include, for example, zopolrestat, epalrestat, ranirestat, berberine and sorbinil, as described in, e.g., U.S. Pat. Nos. 4,939,140; 6,159,976; and 6,570,013. Preferably, the $2^{nd}$ aldose reductase inhibitor is selected from ponalrestat, epalrestat, sorbinil or sorbinol, imirestat, AND-138, CT-112, zopolrestat, zenarestat, BAL-AR18, AD-5467, M-79175, tolrestat, alconil, statil, berberine or SPR-210.

Other therapeutic agents that can be administered include, for example corticosteroids, e.g., prednisone, methylprednisolone, dexamethasone, or triamcinalone acetinide, or noncorticosteroid anti-inflammatory compounds, such as ibuprofen or flubiproben. Similarly, vitamins and minerals, e.g., zinc, and micronutrients can be co-administered. In addition, inhibitors of the protein tyrosine kinase pathway, which include natural protein tyrosine kinase inhibitors like quercetin, lavendustin A, erbstatin and herbimycin A, and synthetic protein tyrosine kinase inhibitors like tyrphostins (e.g., AG490, AG17, AG213 (RG50864), AG18, AG82, AG494, AG825, AG879, AG1112, AG1296, AG1478, AG126, RG13022, RG14620 and AG555), dihydroxy- and dimethoxybenzylidene malononitrile, analogs of lavendustin A (e.g., AG814 and AG957), quinazolines (e.g., AG1478), 4,5-dianilinophthalimides, and thiazolidinediones, can be co-administered with genistein or an analog, prodrug or pharmaceutically acceptable salt thereof (see Levitzki et al., Science 267: 1782-1788 (1995); and Cunningham et al., Anti-Cancer Drug Design 7: 365-384 (1992)). In this regard, potentially useful derivatives of genistein include those set forth in Mazurek et al., U.S. Pat. No. 5,637,703. Selenoindoles (2-thioindoles) and related disulfide selenides, such as those described in Dobrusin et al., U.S. Pat. No. 5,464,961, are useful protein tyrosine kinase inhibitors. Neutralizing proteins to growth factors, such as a monoclonal antibody that is specific for a given growth factor, e.g., VEGF (for an example, see Aiello et al., *PNAS USA* 92: 10457-10461 (1995)), or phosphotyrosine (Dhar et al., *Mol. Pharmacol.* 37: 519-525 (1990)), can be co-administered. Other various compounds that can be co-administered include inhibitors of protein kinase C (see, e.g., U.S. Pat. Nos. 5,719,175 and 5,710,145), cytokine modulators, an endothelial cell-specific inhibitor of proliferation, e.g., thrombospondins, an endothelial cell-specific inhibitory growth factor, e.g., TNFα, an anti-proliferative peptide, e.g., SPARC and prolferin-like peptides, a glutamate receptor antagonist, aminoguanidine, an angiotensin-converting enzyme inhibitor, e.g., angiotensin II, calcium channel blockers, γ-tectorigenin, ST638, somatostatin analogues, e.g., SMS 201-995, monosialoganglioside GM1, ticlopidine, neurotrophic growth factors, methyl-2,5-dihydroxycinnamate, an angiogenesis inhibitor, e.g., recombinant EPO, a sulphonylurea oral hypoglycemic agent, e.g., gliclazide (non-insulin-dependent diabetes), ST638 (Asahi et al., *FEBS Letter* 309: 10-14 (1992)), thalidomide, nicardipine hydrochloride, aspirin, piceatannol, staurosporine, adriamycin, epiderstatin, (+)-aeroplysinin-1, phenazocine, halomethyl ketones, anti-lipidemic agents, e.g., etofibrate, chlorpromazine, spinghosines and retinoic acid and analogs thereof (Burke et al., *Drugs of the Future* 17 (2): 119-131 (1992); and Tomlinson et al., *Pharmac. Ther.* 54: 151-194 (1992)).

V. Diagnostic Applications

The disclosure further relates to diagnosing or prognosticating the risk of developing galactosemia in a subject by measuring one or more biomarkers associated with galactosemia. In one embodiment, the biomarker associated with galactosemia is increased galactitol levels in a biological sample obtained from a subject. Diagnosis may be performed, e.g., by detecting elevated levels of sugar metabolites, e.g., metabolites of galactose (e.g., galactitol) and/or glucose (e.g., sorbitol) in the biological sample, e.g., aqueous or vitreous humor of the eye, blood tissue, cerebrospinal fluid, urine, etc.

Tables 1 and 2 show concentrations of galactose and metabolites thereof in plasma (or whole blood), erythrocyte, and/or urine samples of subjects with classic galactosemia (GALT deficiency) or severe GALK deficiency.

The disclosure further relates to methods for combined diagnosis and intervention of galactosemia, wherein, diagnosis of galactosemia is carried out as described previously via detection of one or more biomarkers in a sample obtained from the subject. Based on the results of the diagnosis, if the subject is determined to have or deemed to be at risk of developing galactosemia, then a composition comprising an aldose reductase inhibitor (ARI) is administered to the subject. Preferably, the ARI comprises a compound of the instant disclosure or a composition comprising the compound of the instant disclosure.

In certain embodiments, the present disclosure provides a method for treating galactosemia, comprising diagnosing a subject for galactosemia by detecting elevated plasma galactitol concentration (e.g., >10 µM galactitol) and/or elevated urinary galactitol levels (e.g., >100 mmol galactitol/mol of creatine); and administering to the galactosemic subject in need thereof, an therapeutically effective amount of a composition that inhibits aldose reductase activity. In another embodiment, the diagnosis step may further comprise a genetic test, e.g., detecting a mutation in one or more of the enzymes involved in Leloir pathway (e.g., GALT, GALK, GALE, etc.). In yet another embodiment, the diagnosis step may additionally comprise conducting an enzymatic assay, e.g., an assay for GALT, GALK, and/or GALE activity using detectable substrates, the products of which may be detected using routine methods, e.g., HPLC or mass spectrometry (Ko et al., *Clinical Chemistry* 56:5 764-771, 2010).

The present disclosure further provides for the use of the compounds of Formula I-VI, or a pharmaceutically acceptable salt, hydrate, solvate, or prodrug thereof, in a method of treating a disease state, and/or condition caused by or related to galactosemia. In another embodiment, the disclosure relates to use of the compounds of Formula I-VI, or a pharmaceutically acceptable salt, hydrate, solvate, or prodrug thereof, in a method of treating a disease state, and/or condition caused by or related to galactosemia, comprising the steps of: (a) identifying a subject in need of such treatment; (b) providing a compound of Formula I-VI, or a pharmaceutically acceptable salt, hydrate, solvate, prodrug thereof; and (c) administering said compound of Formula I-VI in a therapeutically effective amount to treat, suppress and/or prevent the disease state or condition in a subject in need of such treatment.

In another embodiment, the disclosure relates to use of the compounds of Formula I-VI, or a pharmaceutically acceptable salt, hydrate, solvate, or prodrug thereof, in a method of treating a disease state, and/or condition caused by or related to galactosemia, comprising the steps of: (a) identifying a subject in need of such treatment; (ii) providing a composition comprising a compound of Formula I-VI, or a pharmaceutically acceptable salt, hydrate, solvate, prodrug or tautomer thereof; and (iii) administering said composition in a therapeutically effective amount to treat, suppress and/or prevent the disease state or condition in a subject in need of such treatment.

In the aforementioned embodiments, the compound or composition is preferably used orally.

EXAMPLES

The structures, materials, compositions, and methods described herein are intended to be representative examples of the disclosure, and it will be understood that the scope of the disclosure is not limited by the scope of the examples. Those skilled in the art will recognize that the disclosure may be practiced with variations on the disclosed structures, materials, compositions and methods, and such variations are regarded as within the ambit of the disclosure.

Rats, with impaired GALT activity due to genetic modification (GALT null), were used as a model of galactosemia. This rat model mirrors human classic galactosemia in some important ways. The rats develop physical characteristics including cataracts follow exposure to galactose, growth abnormalities, and neurological/cognitive abnormalities, which mirror abnormalities in human patients and can be quantified. The rats also have biochemical characteristics that mirror human disease including elevated levels of galactose and galactose metabolites, including galactitol and Gal1), in blood and tissues.

The rats will be fed a diet containing one or more aldose reductase inhibitors (ARIs), and the effect of AR inhibition will be assayed at the tissue level and also at the in vivo level. For instance, galactitol levels in the eye of GALT-deficient rats may be measured pre- and post-treatment with the ARIs disclosed herein. Alternately or additionally, the effect of ARIs in reducing the frequency and severity of galactosemia and/or improving the outcome of the disease (e.g., improved visual, motor or memory skills) will be measured using routine methods.

Example 1

A study was conducted to test the effects of aldose reductase inhibitors (ARI) (Compound A or Compound B) in the rat model of classic galactosemia (GALT-null rats). The effects of aldose reductase inhibitor treatment on key aspects of galactosemia including growth, formation of cataracts, and metabolite levels (galactose & galactitol) in liver and brain and circulation of GALT null rats exposed to maternal milk was analyzed.

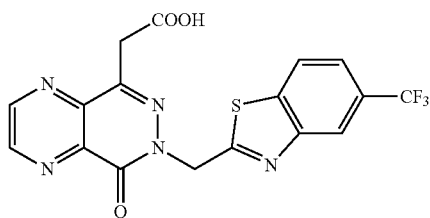

Compound A

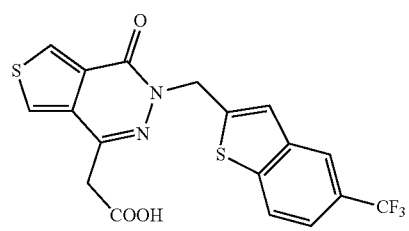

Compound B

Methodology

Genetic Model:

Rats were generated from heterozygote crosses (heterozygous M3 GALT null strain representing classic galactosemia). Wild-type (WT, +/+) and heterozygous rats (+/M3) express normal levels of GALT, whereas M3 homozygotes (M3/M3) do not express GALT at detectable levels, and show aberrantly high levels of galactose and galactitol in liver and brain.

Application of Drug and Placebo:

The vehicle used to administer the drug to newborn pups was Gerber Good Start Birth-12 Months soy formula prepared according to the manufacturer's instructions (157.5 mg powder added to 1 ml deionized water and mixed well before use). Liquid formula was prepared fresh from powder each day and stored at 4° C. until use. Liquid formula alone (no drug powder added) served as a placebo control.

Aldose reductase inhibitor (Compound A or Compound B), suspended in Gerber formula, was administered orally at about 12-hour intervals (BID) at 1 mg inhibitor/gram pup weight (=1000 mg/kg) for each dose. Before use, drug was stored at −20° C. in a bottle or tubes wrapped in aluminum foil. Just before each feeding an aliquot of drug was re-suspended in formula, mixed well, and pipetted into individual tubes to be fed to the pups (volume calculated per pup weight measured that morning). All placebo and drug tubes of formula were warmed to 37° C. immediately before feeding.

Placebo and drug were fed to pups by hand using a syringe and tubing. Pups receiving drug also were fed a small additional volume of Gerber formula that had been used to wash the tube and syringe immediately after the drug feeding. To motivate eating, pups were removed from their mother (to prevent nursing) and maintained in nests in a humidified incubator for about 2 hours at 35-37° C. prior to each feeding. Separate syringes were used for placebo and drug. Pups were wrapped in fleece during feeding, which lasted about 2-5 minutes each.

Tracking Growth:

Growth was tracked (in grams) by weighing each pup every day.

Tracking/Quantifying Cataracts:

In the first part of the study, cataracts were scored visually by a blinded rater on a 3 point scale, with zero being no cataracts present (absent), 1 being mild, 2 being moderate and 3 being severe cataracts present. In the second part of the study, eyes were dissected after euthanization, photographed via digital camera, and cataracts were quantified via software Determining Genotypes:

Pup GALT genotypes (M3/M3 versus M3/+ versus+/+) were determined by Transnetyx using DNA isolated from tail snips collected from all pups at between 5-8 days after birth. Genotypes were corroborated in representative pups by GALT enzyme activity measured in liver samples harvested from pups after euthanasia. In all samples tested, the GALT activity observed was consistent with the GALT genotype.

Euthanizing Pups:

Pups were euthanized by $CO_2$ inhalation according to standard procedures.

Enzyme Assays:

Galactose-1-P uridylyltransferase (GALT) and galactokinase (GALK) assays were performed as described previously (Sanders et al., *Dis Model Mech.*, 3(9-10):628-38, 2010) using lysates prepared from frozen samples of liver. GALK assays were performed as a control for integrity of the samples. Lysates were prepared by homogenizing small pieces (10-50 mg) of liver in 100 µl of lysis buffer consisting of one complete mini protease inhibitor cocktail tablet, EDTA-free (Roche, REF 04 693 159 001) dissolved in 10 ml of 100 mM glycine, pH 8.7. The lysates were centrifuged at 16,110×g for 5 mins at 4° C., and the resulting supernatant was passed over a MICRO BIO-SPIN P-6 chromatography column (Bio-Rad, Inc.) to remove small molecules. Protein concentrations were determined for each sample using the BIO-RAD DC protein assay with BSA as the standard. GALT and GALK assays were run using 4 µg of total protein per reaction. Substrates and products were quantified by HPLC as described previously (Ross, 2004).

Metabolites:

Lysates for metabolite analysis were prepared as follows: 50-100 mg pieces of previously frozen liver or brain were homogenized by grinding for 30 seconds using a Teflon micropestle and handheld micropestle motor (Kimble Chase Life Science and Research Products LLC) in 125 µl ice-cold HPLC-grade water. Metabolites were separated and quantified by HPLC (See, e.g., Daenzer, et al. Dis. Model Mech. 2016, 9(11):1375-1382)). Galactitol, inositol, and glucose were quantified using the same HPLC conditions described to quantify galactose by (Daenzer, 2016). Metabolite levels were normalized to the total area of peaks detected by the relevant column and elution run for that sample, minus the peaks that most distinguished homozygous M3/M3 samples from controls. Specifically, metabolites separated on the MA1 column (galactitol, inositol, galactose and glucose) were normalized to total peak area minus galactose and galactitol, and metabolites separated on the PA10 column (galactose-1P) were normalized to total peak area minus galactose and galactose-1P.

Results

Observations from the in-Life Period:

Though formula with drug was slightly "thicker" in consistency than formula alone, pups consumed both without apparent objection.

Growth:

Pups were weighed each morning and mass was recorded the in grams. The masses of pups that were still gaining weight are presented in FIG. 1. As illustrated, weights of homozygous GALT null pups tended to lag behind their wild-type and heterozygous GALT+ littermates, but the difference was subtle. Other studies have demonstrated that the lag becomes more pronounced and statistically significant after the 3rd week of life.

The data presented in FIG. 1 indicate that drug treatment can reduce or prevent the growth lag in homozygotes.

Cataracts:

Cataracts are the most obvious and visible phenotype associated with GALT-null status in the rat model. The rats open their eyes at day 14 of life with bilateral cataracts present. Of note, infants with classic galactosemia exposed to dietary galactose (e.g., breast milk) also develop bilateral cataracts. In the GALT null rat model, absent intervention, cataracts are seen in all M3/M3 homozygous pups but not in any M3/+ or +/+ pups. In an initial study, cataracts were qualitatively assessed in GALT null rats that were treated with Compound A or placebo at day nine of life. The qualitative assessment was on a scale of 0-3 with 0 indicating cataracts were absent and 3 indicating severe cataracts. As shown in FIG. 2A GALT null rats that were treated with placebo developed sever cataracts by day nine of live. In contrast GALT null rats treated with Compound A had no cataracts. A follow-on study was performed in which rats were treated with Compound A at 1,000 mg/kg BID or 250 mg/kg BID and eyes were digitally photographed and cataracts were quantified. In both studies, Compound A reduced cataracts.

Figure 2B:
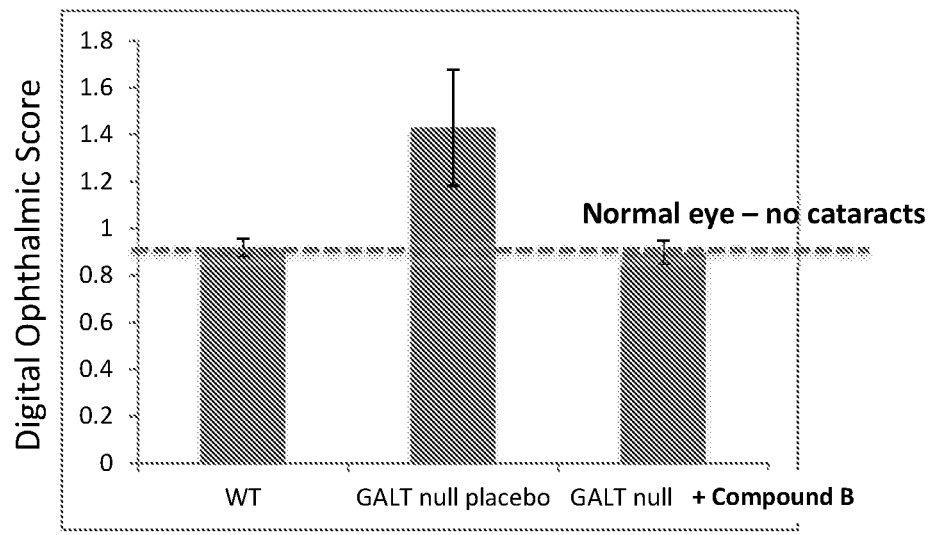
Figure 2C:
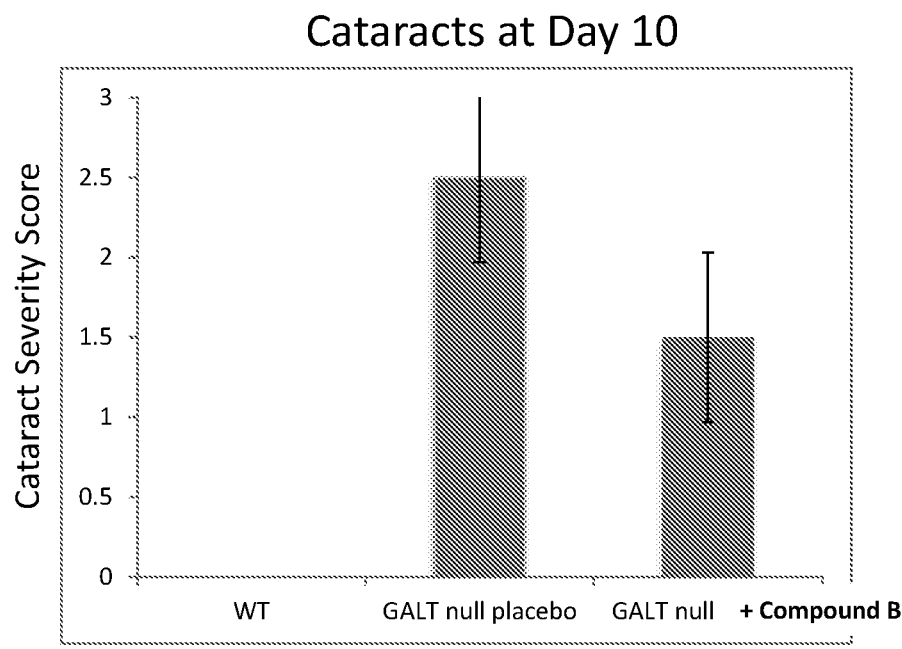
Figure 2D:
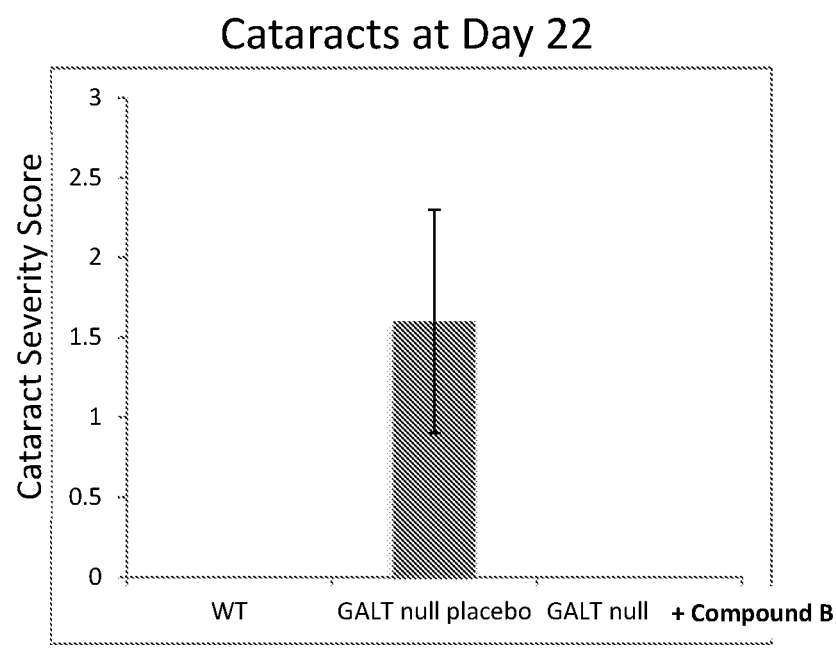

Additional studies were conducted using Compound B, and cataracts were assessed at day 22 of life. Qualitative assessment on the 0-3 scale, show that in this study GALT null rats treated with placebo developed cataracts with average severity of 1.5, but wild type rats and GALT null rats treated with Compound B did not have cataracts (FIG. 2D). Digital quantitative analysis produced the same results, with GALT null rats treated with Compound B having the same score as wild type rats, but GALT null rats treating with placebo having a higher score indicative of cataracts. (FIG. 2B)

Since GALT null rats have cataracts when they open their eyes on day 14 of life, it is possible that treatment of new born rats with aldose reductase inhibitors prevents the formation of cataracts in the post-natal period and/or reduces cataracts that formed in utero. A further study using Compound B, provided evidence that aldose reductase inhibitors can reduce cataracts that are already formed. In this study, cataracts were assessed at days 10 and 22 of life. As shown in FIG. 2C and FIG. 2D, GALT null rats treated with placebo had cataracts at day 10 and at day 22. However, GALT null rats treated with Compound B had cataracts at day 10, but cataracts were not present at day 22. The data demonstrate that treatment with aldose reductase inhibitors can reduce and resolve cataracts.

Metabolites:

Galactose and galactitol metabolites were resolved and quantified via HPLC in samples of both liver and brain from euthanized pups. Treatment with Compound A reduced liver galactitol levels by 87% compared to placebo in GALT null rats at day 9 and by 57% at day 15-18. Treatment with Compound A reduced brain galactitol levels by 40% compared to placebo in GALT null rats at day 9 and by 57% at day 15-18. Additional studies were conducted in rats treating using Compound B, and galactose and galactitol levels were measured at day 10 of life. The results of this study showed that GALT null rats had elevated levels of galactitol in the liver, brain and plasma in comparison to wild type rats. Treatment with Compound B reduced galactitol levels in GALT null rats to normal or near normal levels. (FIG. 3A). The GALT null rats also had elevated galactose and Gal1P levels, relative to wild type rats. Treatment with Compound B did not further increase the galactose or Gal1P levels in the GALT null rats. (FIG. 3B, and FIG. 3C). The data demonstrate that aldose reductase inhibitors can reduce and normalize galactitol levels in affected animals, but does not further elevate galactose and Gal1P levels.

Conclusions and Discussion

This study examined the effects of Aldose Reductase inhibitor exposure (Compound A or Compound B) on growth, cataract formation and galactitol accumulation in GALT-null rat pups. As expected, milk-exposed GALT null animals accumulated dramatically elevated galactose and galactitol in both liver and brain relative to GALT+ heterozygotes or wild-type animals. Treatment with aldose reductase inhibitors significantly lowered galactitol in brain, liver and blood (plasma). Treatment with aldose reductase inhibitor also had dramatic effects on cataracts, and demonstrate that aldose reductase inhibitors can reduce existing cataract to the point where cataract in no longer present. These data demonstrate that aldose reductase inhibitors can be administered to effectively treat galactosemia.

Example 2

In this study longer-term cognitive and neurological deficiencies associated with galactosemia will be studied in GALT null rats and normal control rats that are treated with placebo or with aldose reductase inhibitor. The aldose reductase inhibitors will be administered substantially as described in Example 1, and rats will be evaluated for central nervous system outcomes using rotarod testing, to assess balance, motor control and learning, as well as using novel object recognition testing, to assess cognition and memory. GALT null rats show altered responses in these tests in comparison to wild type rats. The data will show that treatment with aldose reductase inhibitor decreased cognitive and neurological deficiencies of GALT null rats, and that some or all responses of GALT null rats were normalized to the responses observed in wild type rats.

Example 3

A newborn child is diagnosed with classical galactosemia by neonatal testing and presents with elevated blood galactose and galactitol levels. The child is immediately place on a galactose and lactose restricted diet. Therapy with an aldose reductase inhibitor (such as Compound A or Compound B) is initiated at a dose selected by the clinician to normalize blood galactose and/or galactitol levels. Treatment results in reduction and eventual normalization of blood galactitol levels. The child continues therapy indefinitely and periodic checks confirm that blood galactitol levels remain normal. Dosing is adjusted as needed to maintain normal blood galactitol levels. The child does not exhibit growth delay, delayed speech, impaired learning, motor ataxia or presenile cataracts as she ages.

Example 4

An adult patient with galactosemia presents with motor ataxia, spasticity and poor balance. Therapy with an aldose reductase inhibitor (such as Compound A or Compound B) is initiated at a dose selected by the clinician to normalize blood galactose and/or galactitol levels. Treatment results in reduction and eventual normalization of blood galactitol levels. As galactitol levels normalize, the patient exhibits decreased motor ataxia and spasticity, and improved balance. Dosing is adjusted as needed to maintain normal blood galactitol levels, and improvements in the patient's motor control and balance.

Unless otherwise defined, all technical and scientific terms used herein have the same meaning as commonly understood by one of ordinary skill in the art to which this disclosure belongs.

Although methods and materials similar or equivalent to those described herein can be used in the practice or testing of the present disclosure, suitable methods and materials are described in the foregoing paragraphs. In addition, the materials, methods, and examples are illustrative only and not intended to be limiting. All United States patents and published or unpublished United States patent applications cited herein are incorporated by reference. All published foreign patents and patent applications cited herein are hereby incorporated by reference. All published references, documents, manuscripts, scientific literature cited herein are hereby incorporated by reference. All identifier and accession numbers pertaining to scientific databases referenced herein (e.g., PUBMED, NCBI, GENBANK, EBI) are hereby incorporated by reference.

I claim:

1. A method of treating galactosemia or preventing complications associated with galactosemia, comprising administering a therapeutically effective amount of an aldose reductase inhibitor to a subject in need thereof, wherein the aldose reductase inhibitor is a compound of Formula (III) or pharmaceutically acceptable salt thereof:

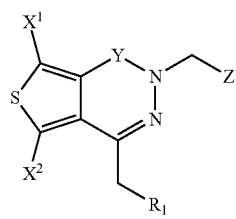

(III)

wherein, $R^1$ is $CO_2R^2$;

$R^2$ is H, $(C_1-C_6)$-alkyl, $(C_1-C_6)$-hydroxyalkyl, or $(C_1-C_6)$-aminoalkyl;

$X^1$ is H or halogen;

$X^2$ is H or halogen;

Y is a bond, C=O, C=S, C=NH, or C=N($C_1-C_4$)-alkyl;

Z is

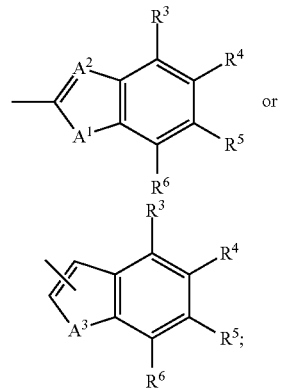

$A^1$ is $NR^7$, O, S or $CH_2$;

$A^2$ is N or CH;

$A^3$ is $NR^7$, O, or S;

$R^3$, $R^4$, $R^5$, and $R^6$ are independently hydrogen, halogen, cyano, acyl, haloalkyl, haloalkoxy, haloalkylthio, trifluoroacetyl, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkyl sulfonyl; and $R^7$ is hydrogen, $C_1-C_4$-alkyl, or $C(O)O$—$(C_1-C_4)$-alkyl.

2. A method of reducing the amount or level of galactitol in a subject with galactosemia, comprising administering a therapeutically effective amount of an aldose reductase inhibitor to the subject, wherein the aldose reductase inhibitor is a compound of Formula (III) or pharmaceutically acceptable salt thereof:

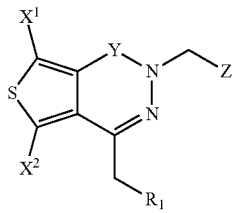
(III)

wherein, $R^1$ is $CO_2R^2$;

$R^2$ is H, $(C_1$-$C_6)$-alkyl, $(C_1$-$C_6)$-hydroxyalkyl, or $(C_1$-$C_6)$-aminoalkyl;

$X^1$ is H or halogen;

$X^2$ is H or halogen;

Y is a bond, C=O, C=S, C=NH, or C=N($C_1$-$C_4$)-alkyl;

Z is

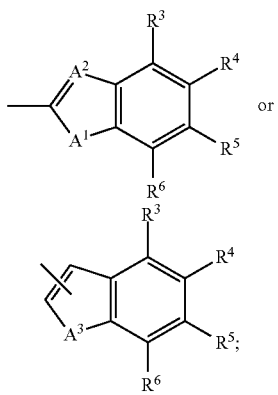

$A^1$ is $NR^7$, O, S or $CH_2$;

$A^2$ is N or CH;

$A^3$ is $NR^7$, O, or S;

$R^3$, $R^4$, $R^5$, and $R^6$ are independently hydrogen, halogen, cyano, acyl, haloalkyl, haloalkoxy, haloalkylthio, trifluoroacetyl, $(C_1$-$C_4)$-alkyl, $(C_1$-$C_4)$-alkoxy, $(C_1$-$C_4)$-alkylthio, $(C_1$-$C_4)$-alkylsulfinyl, or $(C_1$-$C_4)$-alkyl sulfonyl; and $R^7$ is hydrogen, $C_1$-$C_4$-alkyl, or C(O)O—$(C_1$-$C_4)$-alkyl.

3. A method for treating cataracts, comprising administering a therapeutically effective amount of an aldose reductase inhibitor to a subject in need thereof, wherein the aldose reductase inhibitor is a compound of Formula (III) or pharmaceutically acceptable salt thereof:

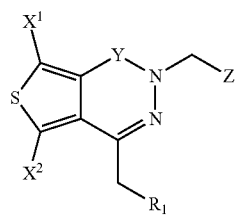
(III)

wherein, $R^1$ is $CO_2R^2$;

$R^2$ is H, $(C_1$-$C_6)$-hydroxyalkyl, or $(C_1$-$C_6)$-aminoalkyl;

$X^1$ is H or halogen;

$X^2$ is H or halogen;

Y is a bond, C=O, C=S, C=NH, or C=N($C_1$-$C_4$)-alkyl;

Z is

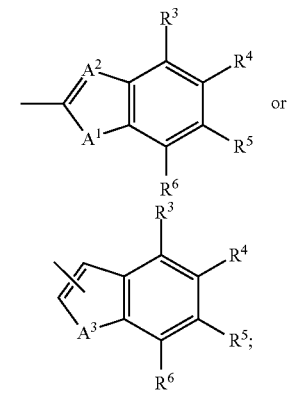

$A^1$ is $NR^7$, O, S or $CH_2$;

$A^2$ is N or CH;

$A^3$ is $NR^7$, O, or S;

$R^3$, $R^4$, $R^5$, and $R^6$ are independently hydrogen, halogen, cyano, acyl, haloalkyl, haloalkoxy, haloalkylthio, trifluoroacetyl, $(C_1$-$C_4)$-alkyl, $(C_1$-$C_4)$-alkoxy, $(C_1$-$C_4)$-alkylthio, $(C_1$-$C_4)$-alkylsulfinyl, or $(C_1$-$C_4)$-alkyl sulfonyl; and $R^7$ is hydrogen, $C_1$-$C_4$-alkyl, or C(O)O—$(C_1$-$C_4)$-alkyl.

4. The method of claim 3, where the subject in need thereof has galactosemia.

5. A method for treating or preventing cognitive or neurological deficiency associated with galactosemia, comprising administering a therapeutically effective amount of an aldose reductase inhibitor to a subject with galactosemia, wherein the aldose reductase inhibitor is a compound of Formula (III) or pharmaceutically acceptable salt thereof:

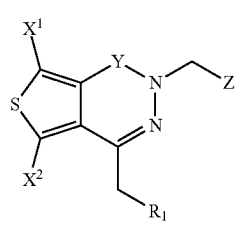
(III)

wherein,
$R^1$ is $CO_2R^2$;
$R^2$ is H, $(C_1-C_6)$-hydroxyalkyl, or $(C_1-C_6)$-aminoalkyl;
$X^1$ is H or halogen;
$X^2$ is H or halogen;
Y is a bond, C=O, C=S, C=NH, or C=N($C_1-C_4$)-alkyl;
Z is

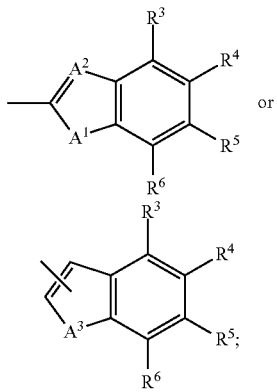

$A^1$ is $NR^7$, O, S or $CH_2$;
$A^2$ is N or CH;
$A^3$ is $NR^7$, O, or S;
$R^3$, $R^4$, $R^5$, and $R^6$ are independently hydrogen, halogen, cyano, acyl, haloalkyl, haloalkoxy, haloalkylthio, trifluoroacetyl, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkyl sulfonyl; and
$R^7$ is hydrogen, $C_1-C_4$-alkyl, or C(O)O—$(C_1-C_4)$-alkyl.

6. The method of claim 5, wherein the cognitive or neurological deficiency associated with galactosemia is speech dysfunction.

7. The method of claim 5, wherein the cognitive or neurological deficiency associated with galactosemia is motor ataxia.

8. The method of claim 5, wherein the cognitive or neurological deficiency associated with galactosemia is cognitive dysfunction.

9. The method of claim 5, wherein the cognitive or neurological deficiency associated with galactosemia is pseudomotor cerebrii.

10. The method of claim 5, wherein the cognitive or neurological deficiency associated with galactosemia is seizure.

11. The method of claim 1, wherein the aldose reductase inhibitor is a compound of Formula (III-1) or pharmaceutically acceptable salt thereof:

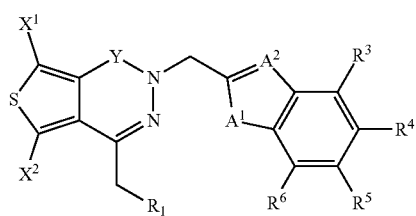

wherein, $R^1$ is $CO_2R^2$;
$R^2$ is H;
$X^1$ is H;
$X^2$ is H;
Y is C=O;
$A^1$ is S;
$A^2$ is N; and
$R^3$, $R^4$, $R^5$, and $R^6$ are independently hydrogen, halogen, or haloalkyl.

12. The method of claim 2, wherein the aldose reductase inhibitor is a compound of Formula (III-1) or pharmaceutically acceptable salt thereof:

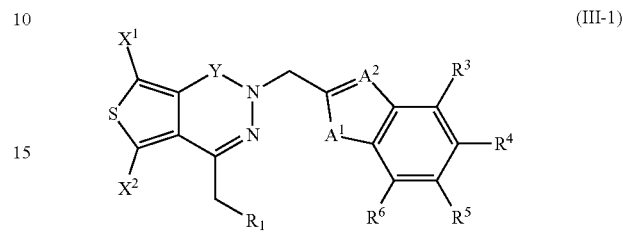

wherein, $R^1$ is $CO_2R^2$;
$R^2$ is H;
$X^1$ is H;
$X^2$ is H;
Y is C=O;
$A^1$ is S;
$A^2$ is N; and
$R^3$, $R^4$, $R^5$, and $R^6$ are independently hydrogen, halogen, or haloalkyl.

13. The method of claim 3, wherein the aldose reductase inhibitor is a compound of Formula (III-1) or pharmaceutically acceptable salt thereof:

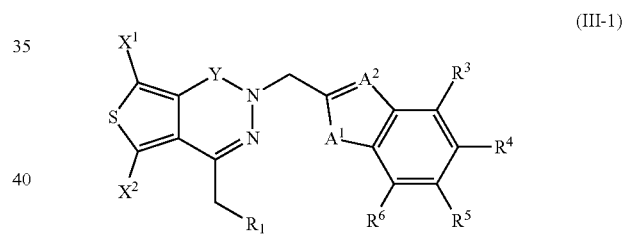

wherein, $R^1$ is $CO_2R^2$;
$R^2$ is H;
$X^1$ is H;
$X^2$ is H;
Y is a C=O;
$A^1$ is S;
$A^2$ is N; and
$R^3$, $R^4$, $R^5$, and $R^6$ are independently hydrogen, halogen, or haloalkyl.

14. The method of claim 5, wherein the aldose reductase inhibitor is a compound of Formula (III-1) or pharmaceutically acceptable salt thereof:

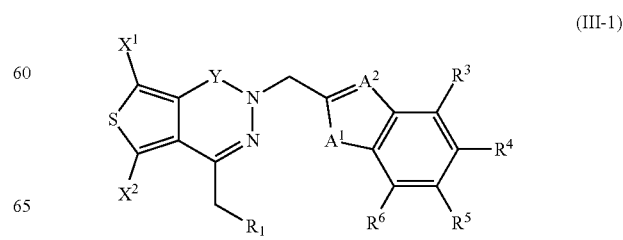

wherein, $R^1$ is $CO_2R^2$;
$R^2$ is H;
$X^1$ is H;
$X^2$ is H;
Y is C=O;
$A^1$ is S;
$A^2$ is N; and
$R^3$, $R^4$, $R^5$, and $R^6$ are independently hydrogen, halogen, or haloalkyl.

15. The method of claim 1, wherein the aldose reductase inhibitor is selected from the group consisting of

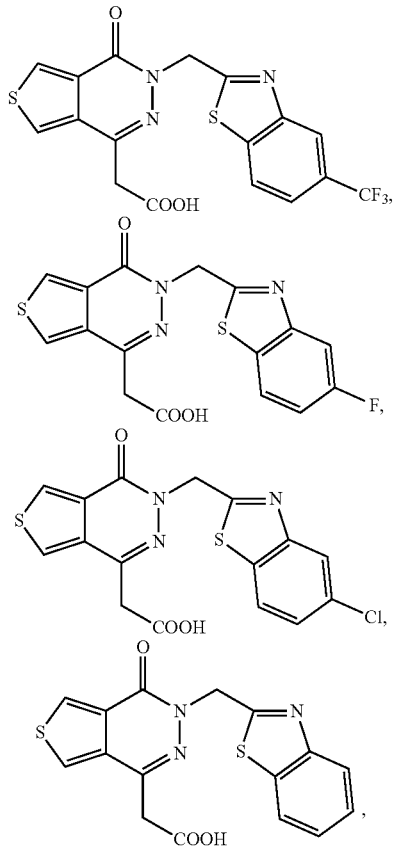

and pharmaceutically acceptable salts thereof.

16. The method of claim 1, wherein the subject is a human.

17. The method of claim 1, wherein the galactosemia is manifested in the subject as increased alditol levels in blood, urine or intraocular fluid.

18. The method of claim 17, wherein the alditol is galactitol, myoinositol or sorbitol.

19. The method of claim 1, wherein the galactosemia is manifested in the subject as increased liver cirrhosis, retinal disorder, macular edema, eye cataract, ovarian dysfunction, muscle or nerve dysfunction, retinopathy, neuropathy, impaired neural conduction or mental retardation.

20. The method of claim 1, wherein the galactosemia is Type I Galactosemia (GALT deficiency).

21. The method of claim 1, wherein the galactosemia is Type II Galactosemia (GALK deficiency).

22. The method of claim 1, wherein the galactosemia is Type III Galactosemia (GALE deficiency).

23. The method of claim 1, wherein the aldose reductase inhibitor is Compound B:

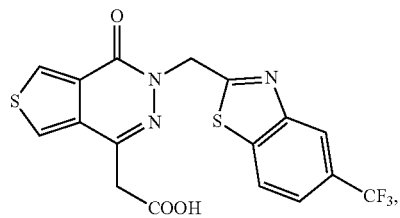

or a pharmaceutically acceptable salt thereof.

24. The method of claim 2, wherein the aldose reductase inhibitor is selected from the group consisting of

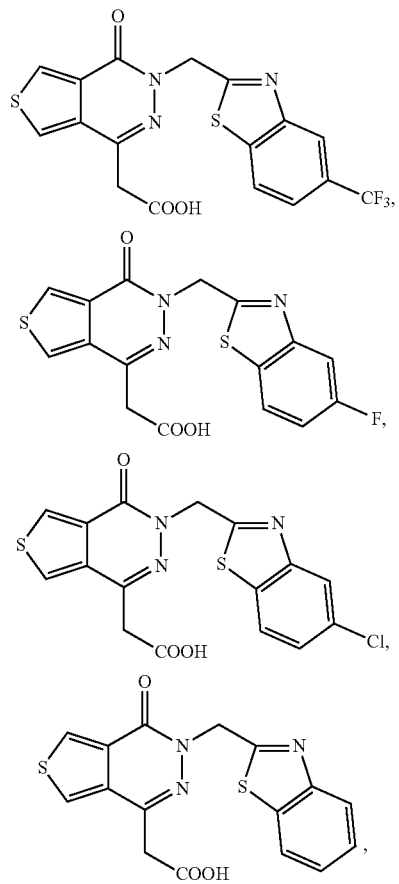

and pharmaceutically acceptable salts thereof.

25. The method of claim 3, wherein the aldose reductase inhibitor is selected from the group consisting of

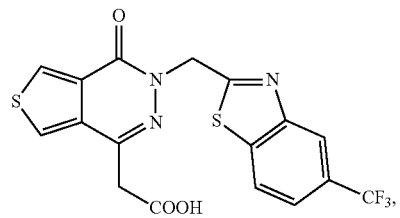

-continued

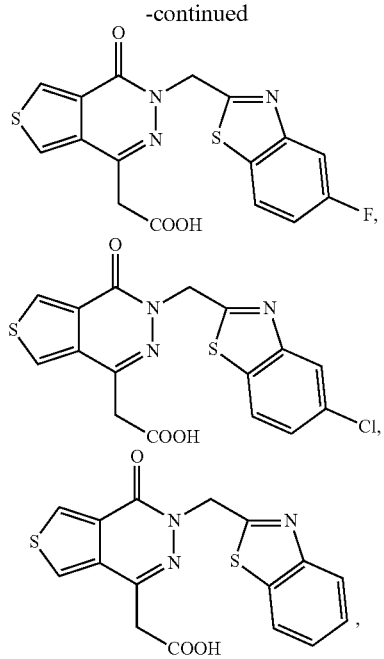

and pharmaceutically acceptable salts thereof.

26. The method of claim 5, wherein the aldose reductase inhibitor is selected from the group consisting of

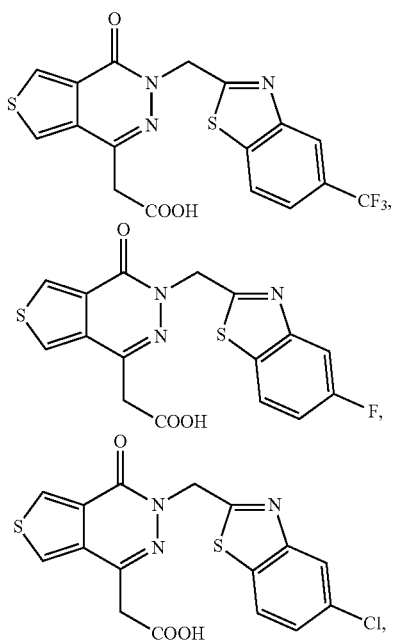

-continued

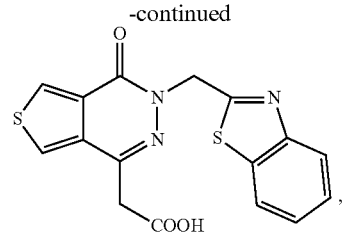

and pharmaceutically acceptable salts thereof.

27. The method of claim 2, wherein the aldose reductase inhibitor is Compound B:

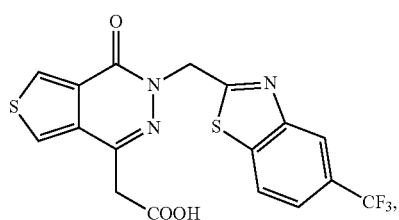 [SMILES: O=C(O)Cc1nn(Cc2nc3cc(C(F)(F)F)ccc3s2)c(=O)c2cscc12]

or a pharmaceutically acceptable salt thereof.

28. The method of claim 3, wherein the aldose reductase inhibitor is Compound B:

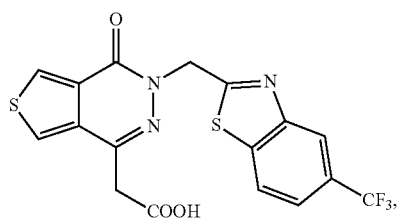 [SMILES: O=C(O)Cc1nn(Cc2nc3cc(C(F)(F)F)ccc3s2)c(=O)c2cscc12]

or a pharmaceutically acceptable salt thereof.

29. The method of claim 5, wherein the aldose reductase inhibitor is Compound B:

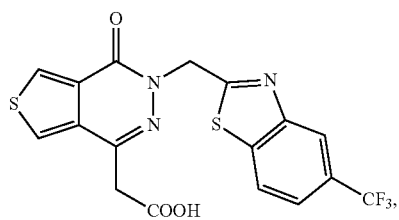 [SMILES: O=C(O)Cc1nn(Cc2nc3cc(C(F)(F)F)ccc3s2)c(=O)c2cscc12]

or a pharmaceutically acceptable salt thereof.

* * * * *

UNITED STATES PATENT AND TRADEMARK OFFICE
CERTIFICATE OF CORRECTION

PATENT NO. : 11,590,131 B2
APPLICATION NO. : 16/634509
DATED : February 28, 2023
INVENTOR(S) : Shoshana Shendelman It is certified that error appears in the above-identified patent and that said Letters Patent is hereby corrected as shown below:

In the Claims

At Column 52, Claim number 3, Line number 14, "$R^2$ is H, $(C_1-C_6)$-hydroxyalkyl, or $(C_1-C_6)$-aminoalkyl;" should read "$R^2$ is H, $(C_1-C_6)$-alkyl, $(C_1-C_6)$-hydroxyalkyl, or $(C_1-C_6)$-aminoalkyl;"

At Column 53, Claim number 5, Line number 3, "$R^2$ is H, $(C_1-C_6)$-hydroxyalkyl, or $(C_1-C_6)$-aminoalkyl;" should read "$R^2$ is H, $(C_1-C_6)$-alkyl, $(C_1-C_6)$-hydroxyalkyl, or $(C_1-C_6)$-aminoalkyl;"

Signed and Sealed this
Nineteenth Day of September, 2023

Katherine Kelly Vidal
*Director of the United States Patent and Trademark Office*